United States Patent
Gretzer et al.

(10) Patent No.: US 9,295,531 B2
(45) Date of Patent: Mar. 29, 2016

(54) COLLAGEN COATED ARTICLE

(75) Inventors: Christina Gretzer, Göteborg (SE); Matthias Mörgelin, Trelleborg (SE)

(73) Assignee: DENTSPLY International Inc., York, PA (US)

( * ) Notice: Subject to any disclaimer, the term of this patent is extended or adjusted under 35 U.S.C. 154(b) by 245 days.

(21) Appl. No.: 13/493,191

(22) Filed: Jun. 11, 2012

(65) Prior Publication Data
US 2012/0316646 A1    Dec. 13, 2012

Related U.S. Application Data

(60) Provisional application No. 61/500,294, filed on Jun. 23, 2011, provisional application No. 61/496,278, filed on Jun. 13, 2011.

(30) Foreign Application Priority Data

Jun. 13, 2011 (EP) ..................................... 11169676
Jun. 23, 2011 (EP) ..................................... 11171146

(51) Int. Cl.
| | |
|---|---|
| *A61F 2/02* | (2006.01) |
| *B32B 9/00* | (2006.01) |
| *C07K 14/78* | (2006.01) |
| *A61F 2/28* | (2006.01) |
| *A61C 8/02* | (2006.01) |
| *A61L 27/24* | (2006.01) |
| *A61L 27/34* | (2006.01) |
| *A61L 31/04* | (2006.01) |
| *A61L 31/10* | (2006.01) |

(52) U.S. Cl.
CPC .............. *A61C 8/0006* (2013.01); *A61L 27/24* (2013.01); *A61L 27/34* (2013.01); *A61L 31/044* (2013.01); *A61L 31/10* (2013.01); *A61F 2310/00982* (2013.01); *Y10T 428/249924* (2015.04)

(58) Field of Classification Search
None
See application file for complete search history.

(56) References Cited

U.S. PATENT DOCUMENTS

| | | | | |
|---|---|---|---|---|
| 4,544,516 A | * | 10/1985 | Hughes et al. ................. | 264/108 |
| 5,002,583 A | * | 3/1991 | Pitaru et al. ................. | 623/11.11 |
| 5,162,430 A | * | 11/1992 | Rhee et al. .................... | 525/54.1 |
| 5,866,113 A | * | 2/1999 | Hendriks et al. ........... | 424/78.17 |
| 2002/0004060 A1 | | 1/2002 | Heublein et al. | |
| 2006/0270037 A1 | | 11/2006 | Kato et al. | |
| 2008/0260794 A1 | | 10/2008 | Lauritzen et al. | |
| 2009/0297581 A1 | | 12/2009 | Atanasoska et al. | |
| 2010/0268227 A1 | | 10/2010 | Tong et al. | |

FOREIGN PATENT DOCUMENTS

| | | |
|---|---|---|
| EP | 0161086 A2 | 11/1985 |
| EP | 0169001 A2 | 1/1986 |
| WO | 9103990 A1 | 4/1991 |
| WO | 2008117954 A1 | 10/2008 |
| WO | 2009036117 A1 | 3/2009 |
| WO | 2009131752 A2 | 10/2009 |
| WO | 2010001149 A2 | 1/2010 |

OTHER PUBLICATIONS

Muller et al. "Surface engineering of stainless steel materials by covalent collagen immobilization to improve implant biocompatibility", Biomaterials, 26, 2005, pp. 6962-6972.*
Spoerke et al. "Synthesis of a poly(L-lysine)-calcium phosphate hybrid on titanium surfaces for enhanced bioactivity", Biomaterials, 26, 2005, pp. 5120-5129.*
Gaudet et al. "Influence of Type I Collagen Surface Density on Fibroblast Spreading, Motility, and Contractility", Biophysical Journal, 85(5), 2003, 3329-3335.*
Yang et al. "Mechanical Properties of Native and Cross-linked Type I Collagen Fibrils", Biophysical Journal, 94(6), 2008, pp. 2204-2211.*
Anselme K. Osteoblast adhesion on biomaterials, Biomaterials 21, 667-681 (2000).
Martin J.Y. et al, Clin Oral Implants Res, Mar. 7(1), 27-37, 1996.
Kieswetter K,et al.,J. Biomed Mater Res, Sep., 32(1), 55-63, 1966.
Muller R., Abke J. Schnell, Scharnweber D, Kujat R, Englert C, Taheri D, Nerlich M, Angele P, Biomaterials 27(22) 4059-68 (2006).
Hao L and Lawrence J, J Mater Sci Mater Med, 2007, 18(5), 807-17.
Chimutengwende-Gordon, M., C, Pendegrass, and G. Blunn, Biomed Mater, 2011.6(2): p. 025008.
Balaban, N.Q., et al.,Nat Cell Biol, 2001. 3(5): p. 466-72.
Stanford, Jacobson et al,1995, Journal of Biological Chemistry 270(16): 9420-9428.
Schneider, Zaharias et al., 2004. Journal of Biomedical Materials Research. 69A 3:462-468.
Morra,M et al;Osteogenic Stimulation of Human Mesenchymal Cells by Collagen-Modified Ti Surfaces;Presented at the 18th annual scientific meeting of the European Assoc. of Osseointegration 2009.
Morra, M..et al;Surface engineering of titanium by collagen immobilization.Surface characeraztion & in vitro & in vivo studies;Biomaterials 24 (2003)4639-4654.

(Continued)

*Primary Examiner* — Bethany Barham
*Assistant Examiner* — Melissa Javier
(74) *Attorney, Agent, or Firm* — David A. Zdurne; Douglas J. Hura; Leana Levin

(57) ABSTRACT

The invention provides a biocompatible article having a surface comprising collagen fibrils attached to said surface via one or more linker molecules, wherein each of said collagen fibrils is attached to at least one of said one or more linker molecules at a proximal end of the fibril, and wherein each of said collagen fibril has a proximal portion extending from said proximal end to a point P along said fibril, wherein, for a majority of said fibrils, each fibril at said point P is oriented so as to form an angle $\alpha_P$ in the range of 0° to 45° to the surface normal N at the point of attachment of said fibril to said surface. The collagen fibril-coated surface has improved biocompatibility and is useful in a medical implant intended for implantation into soft tissue or bone tissue.

35 Claims, 18 Drawing Sheets

(56) References Cited

OTHER PUBLICATIONS

Schuler, Martin et al;Biomimetic modification of titanium dental implant model surfaces using the RGDSP-peptide sequence:A cell morphology study.
Schindler, M Biomaterials. Oct. 2005;26(28):5624-31. Epub Apr. 18, 2005.
Meshel AS Nat Cell Biol. Feb. 2005;7(2):157-64. Epub Jan. 16, 2005.
European Search Report, application No. 11169676.1, Search completed Nov. 10, 2011.
PCT/SE2012/050628 International Search Report.
PCT/SE2012/050628 PCT Written Opinion.
Nebe B. et al., Improved initial osteoblast functions on amino-functionalized titanium surfaces, 2007, Biomolecular Engineering, vol. 24, pp. 447-454; figure 1; Paragraph 2.3.
Sherratt M.J. et al., The morphology of absorbed extracellular matrix assemblies is critically dependent on solution calcium concentration, 2007, Matrix Biology, vol. 26, pp. 156-166; abstract.
Deppe H., et al., Laser-assisted three-dimensional surface modifications of titanium implants: preliminary data, 2005, Lasers in Medical Science, vol. 19, pp. 229-233.

* cited by examiner

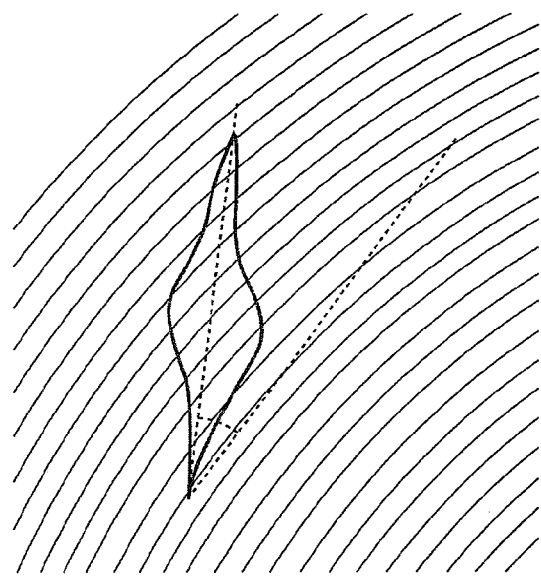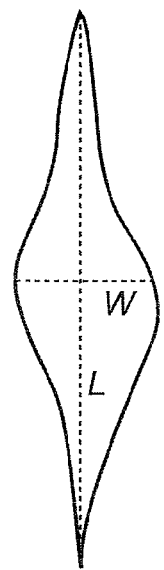
*Fig. 9a*    *Fig. 9b*
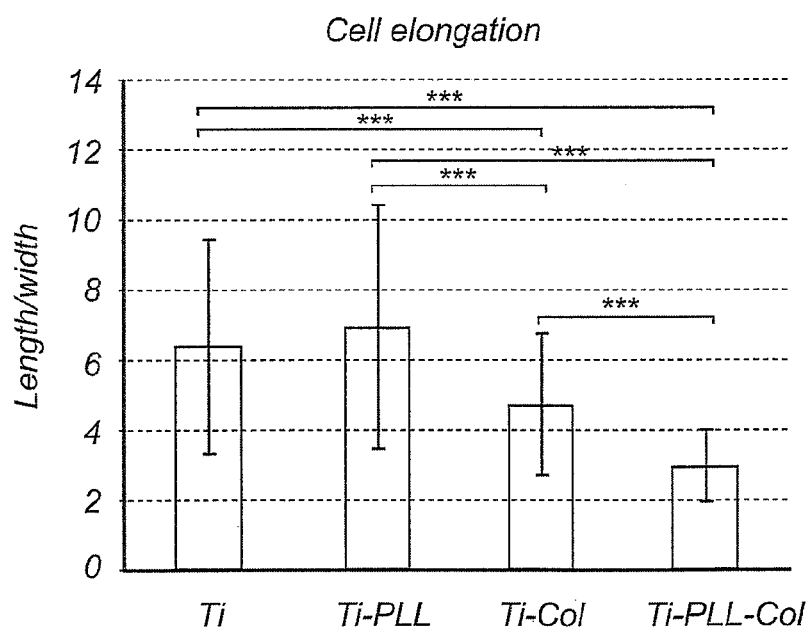
*Fig. 10*

COLLAGEN COATED ARTICLE

RELATED APPLICATIONS

This patent application claims the benefit of and priority to EP Application Ser No. 11169676.1, filed on Jun. 13, 2011, U.S. Provisional Patent Application Ser. No. 61/496,278, filed on Jun. 13, 2011, EP Application Ser No. 11171146.1, filed on Jun. 23, 2011, and U.S. Provisional Patent Application Ser. No. 61/500,294, filed on Jun. 23, 2011, which are herein incorporated by reference for all purposes.

FIELD OF THE INVENTION

The invention relates to a biocompatible article provided with a collagen coating for improving the compatibility with living tissue, and to a method of preparing such an article.

BACKGROUND OF THE INVENTION

Implantable medical devices may be used for treatment, curing or remedy of many diseases and conditions in a patient's body. Implantable medical devices may be used for replacing a part of the body (e.g. dental and orthopaedic implants, intraocular lenses), or may be used to correct or restore the structure of an internal tissue or organ (e.g. vascular stents). Implantable medical devices may also be used as drug delivery vehicles.

For example, dental implant systems are widely used for replacing damaged or lost natural teeth. In such systems, a dental fixture is placed in the upper or lower jawbone of a patient in order to replace the natural tooth root. An abutment structure comprising one or several parts is then attached to the fixture in order to build up a core for the part of the prosthetic tooth protruding from the bone tissue, through the soft gingival tissue and into the mouth of the patient. On said abutment, the prosthesis or crown may finally be seated.

For any type of medical implant, biocompatibility is a crucial issue. The risk for foreign body reaction, clot formation and infection, among many other things, must be addressed and minimized in order to avoid adverse effects, local as well as systemic, which may otherwise compromise the health of the patient and/or lead to failure of the implant.

Healing or regeneration of tissue around an implant is vital in order to secure the implant and its long-term functionality. This is particularly the case for load-bearing implants such as dental or orthopaedic implants. For dental fixtures, a strong attachment between the bone and the implant is necessary.

Formation of bone at an implant surface requires the differentiation of precursor cells into secretory osteoblasts to produce unmineralised extracellular matrix (ECM), and the subsequent calcification of this matrix, as described in for instance Anselme K, Osteoblast adhesion on biomaterials, *Biomaterials* 21, 667-681 (2000). The mechanisms of osseointegration of bone implants have been increasingly elucidated during the last 30 years and today bone implants are particularly designed with respect to material composition, shape and surface properties in order to promote osseointegration. For example, the surface of bone implants is typically provided with a microroughness, which has been demonstrated to affect cell proliferation and differentiation of osteoblast cells, and the local production of growth factors by the cells around a bone implant (Martin J Y et al, *Clin Oral Implants Res*, March 7(1), 27-37, 1996; Kieswetter K, et al., *J Biomed Mater Res*, September, 32(1), 55-63, 1996). Further, the surface of a bone implant and may be chemically modified e.g. by coating with bone-like substances such as hydroxyapatite or by application of other bioactive substances that enhance bone formation. It is known that osteoblasts, i.e., bone-forming cells, sense and react to multiple chemical and physical features of the underlying surface. For example, it has been found that a cross-liked collagen layer on a metallic biomaterial improved the cellular response of human osteoblast-like (MG-63) cells (Müller R, Abke J, Schnell E, Scharnweber D, Kujat R, Englert C, Taheri D, Nerlich M, Angele P, *Biomaterials* 27(22) 059-68 (2006)).

However, a problem with known coatings of e.g. hydroxyapatite or collagen is that the coating may adhere poorly to the implant surface, and may loosen from the implant after implantation, thus compromising its function of enhancing the formation of a strong implant-tissue bond.

For implants intended for contact with soft tissue, such as for example dental implants systems which are to be partially located in the soft gingival tissue, also the compatibility with soft tissue is vital for implant functionality. Typically, after implantation of a dental implant system, an abutment is partially or completely surrounded by gingival tissue. It is desirable that the gingival tissue should heal quickly and firmly around the implant, both for medical and esthetic reasons. A tight sealing between the oral mucosa and the dental implant serves as a soft tissue barrier against the oral microbial environment and is crucial for implant success. This is especially important for patients with poor oral hygiene and/or inadequate bone and mucosal quality. Poor healing or poor attachment between the regenerated tissue and the implant increases the risk for infection and periimplantitis, which may ultimately lead to bone resorption and failure of the implant. Moreover, as the bone is resorbed, the gingiva which is connected to the bone is resorbed as well, resulting in so called "black triangles", i.e. the absence of gingival tissue between two teeth or implants, which is unaesthetic and may give rise to discomfort for the patient. Worse, extensive gingival resorption can expose the outermost part of the implant.

Many strategies have been proposed to promote tissue healing and integration of soft tissue implants. As an example, WO2009/036117 addresses the problem of poor biological and physiological tolerance of medical devices following implantation, and proposes a biological construct for tissue remodeling which mimics the topographical and physiological environment of a natural healing process. The construct comprises a nano-textured, cyto-compatible, layered, biocompatible polymeric biomatrix comprising a polymeric bioscaffold seeded with various therapeutic agents. The bioscaffold may comprise pharmaceutical substances and/or other biologically active agents or cells and is designed to release the therapeutic agents in a temporal order that mimics the order of physiological processes that take place during natural organogenesis and tissue regeneration. The polymeric biomatrix can be affixed e.g. by dipping or ultrasonic spray coating, to a delivery vehicle such as a medical device including a stent, vascular graft, shunt, screw, laminar sheet or mesh. However, the complex structure of the construct of WO 2009/036117 would require a relatively complex, multi-step manufacturing process.

Thus, in spite of the advances made in this field in recent years, there is still a need for improved implantable devices which provide improved short-term tissue response and/or improved long-term tissue integration.

SUMMARY OF THE INVENTION

It is an object of the present invention to at least partially overcome the drawbacks of the prior art, and to provide a biocompatible article having a surface which is capable of further promoting tissue regeneration and improved tissue integration of the article.

In one aspect, the invention provides a biocompatible article having a surface comprising collagen fibrils attached to said surface via one or more linker molecules, wherein the collagen fibrils are oriented substantially vertical to the surface for a major portion of their length. The vertical orientation of the collagen fibrils is believed to contribute to improved biocompatibility of the present article compared to conventional collagen-coated implantable articles. The vertical fibril orientation is achieved by using a linker molecule, such as poly-L-lysine, to which the individual fibrils can attach at an end of the fibril.

In another aspect, the invention provides a biocompatible article having a surface comprising collagen fibrils attached to said surface via one or more linker molecules, wherein each of said collagen fibrils is attached to at least one of said one or more linker molecules at a proximal end of the fibril, and wherein each of said collagen fibril has a proximal portion extending from said proximal end to a point P along said fibril, wherein, for a majority of said fibrils, each fibril at said point P is oriented so as to form an angle $\alpha_P$ in the range of 0° to 45° to the surface normal N at the point of attachment of said fibril to said surface. For example, $\alpha_P$ may be in the range of from 0° to 30°, from 0° to 20°, from 0° to 15°, or from 0° to 10°. The smaller the angle $\alpha_P$, the more vertical is the fibril orientation. Adjacent fibrils, or even all fibrils, typically have approximately the same $\alpha_P$ and point substantially in the same direction. The distal end of the fibril, i.e. the end opposite said proximal end, is typically positioned farther away from the surface than the proximal end.

For example, at least 50%, at least 75% or at least 90%, of the fibrils may have an orientation as described above.

The biocompatible article of the invention, which is useful e.g. as a medical implant, offers improved biocompatibility compared to conventional collagen-coated implantable articles. The present biocompatible article allows faster tissue regeneration (healing) and/or improved tissue-implant attachment. It is believed that the beneficial effects are at least partially due to the three-dimensional fibril orientation on the surface of the article.

In embodiments of the invention, the proximal portion of a fibril comprises a point O along the fibril, located between the proximal end and the point P, wherein the fibril at said point O forms an angle $\alpha_o$ to the surface normal N, and wherein the value of $\alpha_o$ is approximately equal to, or smaller than, the value of $\alpha_P$. For example, $\alpha_O$ may be up to 10° smaller than $\alpha_P$, for example 5° smaller than $\alpha_P$. In some embodiments, the proximal portion may be substantially straight, and in such cases may oriented with an angle $\alpha_1$ in the range of from 0 to 45° in relation to the surface normal at the point of attachment of the fibril to the surface.

In embodiments of the invention, said proximal portion extends at least 5 µm, preferably at least 10 µm, more preferably at least 15 µm, even more preferably at least 20 µm, from said proximal end of the fibril. Since the fibrils may have a length of about 20 µm, this means that they may be directed generally outwards from the surface for a major part, or even all, of their length resulting in a fibril orientation which may attract cells and/or enhance cell activity on the surface.

In embodiments of the invention, said one or more linker molecules bind said collagen fibrils by electrostatic force. Furthermore, alternatively or additionally, the linker molecule may be bound to the surface of the biocompatible article by electrostatic force.

In embodiments of the invention, the linker molecule may be selected from poly-L-lysine, poly-D-lysine, and carbodiimide, and preferably is poly-L-lysine (PLL).

The collagen fibrils used in the present invention may have a diameter in the range of from 50 to 150 nm and a length in the range of from 20 to 200 for example from 20 to 100 µm. Said collagen fibrils are individual collagen fibrils that do not form part of a collagen fiber. Typically, the biocompatible article may have a density of collagen fibrils of 1-50 fibrils/µm² on its surface, for example 2 to 50 fibrils/µm², preferably 5 to 50 fibrils/µm² and more preferably 10 to 50 fibrils/µm².

In embodiments of the invention, the collagen fibrils may comprise collagen type I, and preferably consist of collagen type I. In other embodiments, the collagen fibrils may comprise collagen type II and/or collagen type III.

In embodiments of the invention, the collagen fibrils may comprise non-human, such as bovine or equine, collagen. Alternatively, the collagen fibrils may comprise human collagen. In yet other embodiments, the collagen fibrils may comprise recombinant collagen.

In embodiments of the invention, the surface of the biocompatible article may comprise a metallic material, typically a biocompatible metal such as titanium or alloys thereof. Alternatively, the surface may comprise a ceramic material. Typically, the biocompatible article may comprise a single body having said surface, which body is made of said metallic or ceramic material. Alternatively, the article may comprise particles, each particle having such a surface.

The surface of the biocompatible article onto which the collagen fibrils are attached is typically intended for contact with living cells, in particular living tissue. More particularly, said surface may be intended for contact with living cells that are capable of producing extracellular matrix (ECM) components, such as collagen. It is believed that such cells will be highly responsive to said surface and be stimulated to form new or healed tissue. The surface of the biocompatible article may be intended for contact with soft tissue of with bone tissue.

In another aspect, the present invention provides an implant intended for implantation into the body of a human or animal, comprising a biocompatible article as described herein. For example, the medical device may be a dental implant, such as a dental abutment. It is believed that the collagen fibrils on a gingival-contacting surface of a dental abutment will result in improved early tissue adhesion to the abutment surface and thus reduce the risk for periimplantitis etc. Alternatively, the medical device may be a dental fixture to be inserted into bone tissue. It is believed that the collagen fibrils present on the surface in such cases will promote the osseointegration process by early stimulation of ECM formation.

In another aspect, the invention provides a method of attaching individual collagen fibrils to a surface of a biocompatible article or an implant, comprising the steps of:

i) attaching linker molecules to said surface; and
  ii) attaching individual collagen fibrils to said linker molecules.

Typically the collagen fibrils are attached at one end to the linker molecules, thus allowing a fibril orientation as described above. Hence, the present method may be used to produce a biocompatible article as described herein.

Typically, step i) may be performed by: i-a) applying a solution comprising the linker molecules and a solvent onto the surface of the article, and i-b) removing said solvent. The linker molecules may comprise poly-L-lysine. Step i-b) may comprise e.g. evaporation or rinsing.

Typically, step ii) may be performed by: ii-a) applying a solution comprising individual collagen fibrils and a solvent to said surface, ii-b) incubating the article having said solution applied to said surface, and ii-c) removing said solvent. The solvent may be an aqueous solvent. The solvent may be acidic, and may hence comprising an acid, typically a weak acid such as acetic acid. Furthermore, the solvent may comprise glucose.

Step ii-b) may be performed by keeping the article at a temperature in the range of 4 to 40° C., preferably 15 to 25° C., for at least 10 minutes.

In embodiments of the invention, the solution comprising individual collagen fibrils may have a concentration of collagen fibrils in the range of from 0.1 to 10 mg/ml, preferably 0.5 to 5 mg/ml. Furthermore, after step ii) the density of collagen fibrils on said surface may be in the range of from 1 to 50 fibrils/$\mu m^2$, for example 2 to 50 fibrils/$\mu m^2$, preferably 5 to 50 fibrils/$\mu m^2$ and more preferably 10 to 50 fibrils/$\mu m^2$. Such fibril density may possibly contribute to a straight, outwardly directed fibril orientation. The fibrils may be substantially homogeneously distributed on said surface.

As mentioned above, the collagen fibrils preferably comprise collagen type I.

In another aspect, the present invention relates to the use of a biocompatible article or an implant comprising such an article as described herein, for implantation into a human or an animal. The biocompatible article or implant may be implanted into soft tissue, or into bone tissue. In embodiments of the invention, the biocompatible article or implant may be implanted into a periodontal region of said human or animal.

It is noted that the invention relates to all possible combinations of features recited in the claims.

BRIEF DESCRIPTION OF THE DRAWINGS

FIG. 9a-b is a sketch illustrating how cell alignment and cell elongation was measured;

FIG. 10 is a graph showing the elongation of cells grown on different surfaces;

Figure 1:
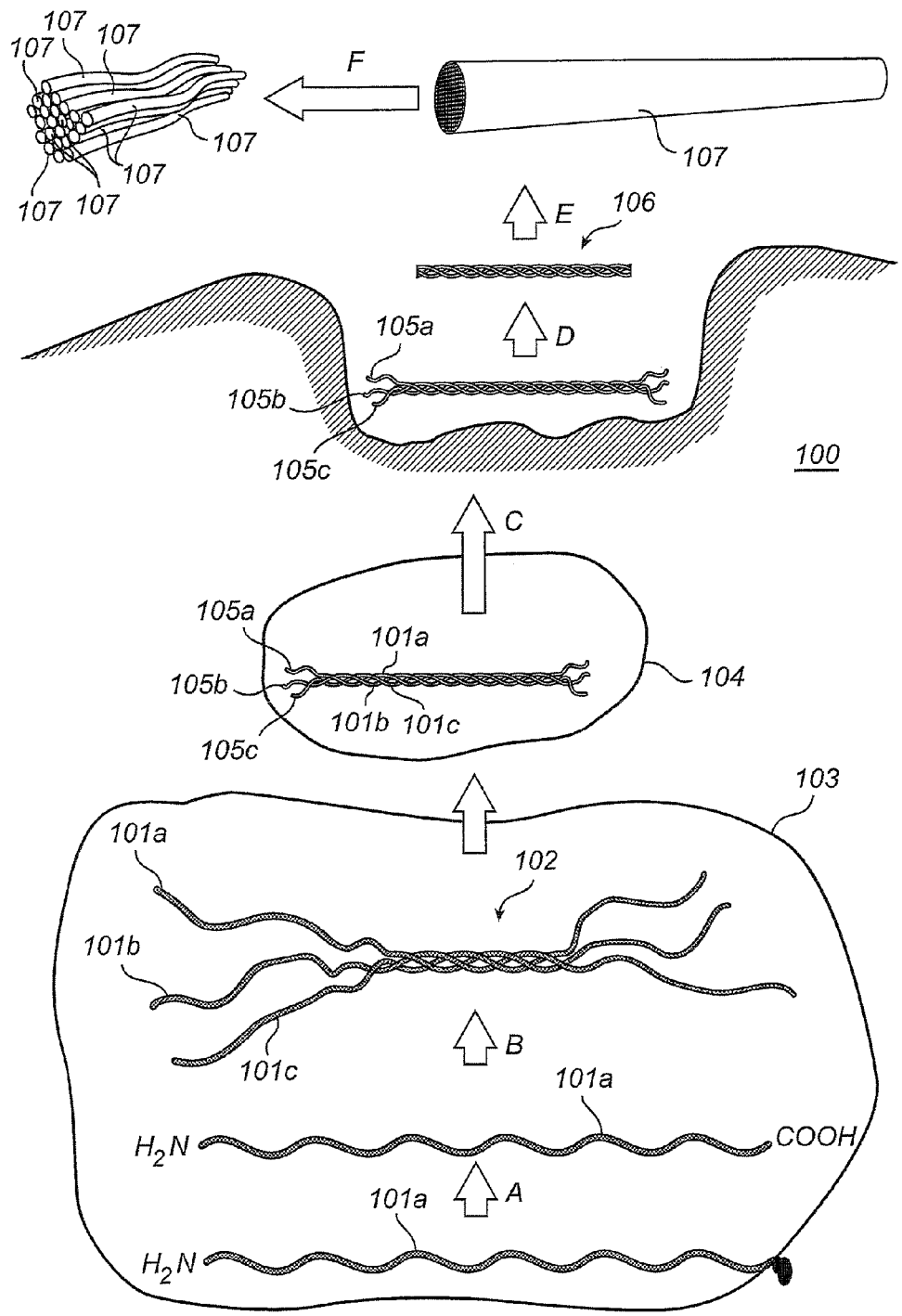
FIG. 1 is a schematic illustration of the collagen synthesis process.

In the figures, the sizes of the fibrils, the linker etc may be exaggerated for illustrative purposes and thus are not drawn to scale.

DETAILED DESCRIPTION OF THE INVENTION

The present inventors have found that collagen fibrils can be attached to a surface, such as the surface of a biocompatible article, in particular a medical implant, in a manner which resembles the orientation or structure of native collagen produced by endogenous cells during the natural tissue regeneration or remodeling process.

As used herein, the term "biocompatible article" includes within its scope any article which is intended for long-term or short-term contact with living cells or tissue and which, upon said contact, does not evoke significant adverse biological reaction of the cells or tissue. One example of a biocompatible article is an implant, such as a dental implant.

As used herein the term "implant" includes within its scope any device of which at least a part is intended to be implanted into the body of a vertebrate animal, in particular a mammal, such as a human. Implants may be used to replace anatomy and/or restore any function of the body. Generally, an implant is composed of one or several implant parts. For instance, a dental implant usually comprises a dental fixture coupled to secondary implant parts, such as an abutment and/or a restoration tooth. However, any device, such as a dental fixture, intended for implantation may alone be referred to as an implant even if other parts are to be connected thereto.

Natural wound healing, e.g. following implantation of an implant, involves many events, many of which overlap or occur simultaneously. Within hours after injury (e.g. surgical trauma), an acute inflammation reaction is initiated at the site of injury. The acute inflammatory phase is characterized by blood clotting, the secretion of inflammatory factors and recruitment of inflammatory cells such as neutrophils and monocytes, which subsequently develop into macrophages, to the wound site. Bacteria and cellular debris are removed, and a preliminary extracellular matrix is formed mainly of fibrin. The provisional fibrin matrix serves as a structure and a substrate for cell adhesion and migration during the inflammatory phase but also for next phase of wound healing, tissue regeneration (proliferation). A few days after injury, macrophages have cleaned the wounded site of debris and also released factors that stimulate angiogenesis and the creation of a new, permanent extracellular matrix. Endothelial cells and fibroblasts are attracted to the wounded area. In soft tissue, fibroblasts, which is the predominant cell type at the wounded site about 1 week following injury, recreate the structural integrity of the tissue by the synthesis of fibronectin, collagen, elastin, glycoproteins, proteoglycans, and glycosaminoglycans, thus forming the new extracellular matrix.

The extracellular matrix provides a scaffold which allows native tissue cells to recreate healthy tissue. At the end of the proliferative phase, myofibroblasts contract the edges of the wound and break down the preliminary matrix formed during inflammation. The tissue remodeling phase that follows involves the simultaneous degradation and synthesis of collagen to produce a strong, mature tissue. In hard tissue such as bone, the healing phase is dominated by osteoblasts forming the new bone tissue including a large portion of native collagen I.

Upon implantation of a medical implant in living tissue, the implant surface is immediately covered with a fluid film containing water and various ions. Next, small sized proteins with high diffusion rate are adsorbed at the implant surface, but are eventually replaced with larger proteins having a higher affinity for the surface (Vroman effect). Lastly, cells will reach and, if the conditions are right, bind to the surface via the adsorbed proteins. Thus, the cells will never sense the naked implant surface but rather a surface with adsorbed biomolecules. Cells bind the surface adsorbed adhesion proteins, such as fibronectin or collagen, via transmembrane receptors called integrins. Integrin binding trigger numerous biological processes which are responsible for cell attachment, spreading and morphology, thus influencing cell behavior at the implant surface and ultimately also the tissue response to the implant.

As used herein, "soft tissue" refers to any tissue type that is not bone or cartilage (referred to as hard tissue). The present invention may be applicable to both soft tissue and hard tissue implantation. In particular, the present invention may be used for implantation in connective tissue, for example mucosa.

Collagen is a protein that forms a major component of the extracellular matrix of many tissues and organs. There are at least ten different types of collagen found in various tissues; collagen type I (collagen I) being the most abundant form in bone and connective tissue; collagen type II being predominant in cartilage, collagen III being a major constituent of the blood vessel wall but also present in cartilage, and collagen type IV being a constituent of the basement membrane.

An individual collagen molecule consists of three polypeptide chains (also referred to as pro $\alpha$-chains), each forming an $\alpha$-helix, closely intertwined in a triple helix configuration.

Different types of collagen differ in the amino acid sequences of the polypeptide chains, and also with respect to secondary structure and/or tertiary structure. In type I collagen, the three-chain helix coils to form a right-handed helix with a pitch of about 100 nm.

Figure 2:
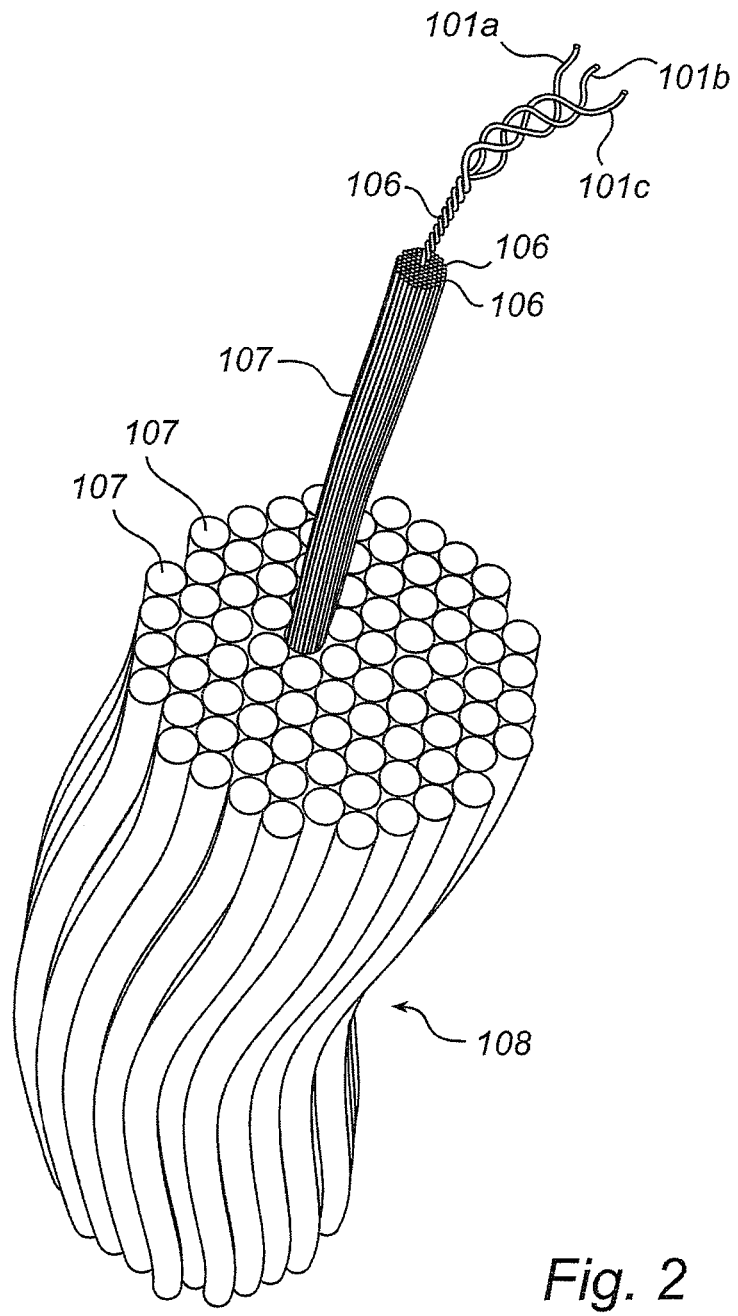
FIG. 2 is a schematic illustration of the hierarchical structure of collagen.

The structure and synthesis of collagen I is schematically illustrated in FIG. 1 and FIG. 2, which use the same reference numbers for identical elements. FIG. 1 illustrates polypeptide chains (pro $\alpha$-chains) 101$a$ being synthesized (step A) in the endoplasmic reticulum 103 of a collagen-producing cell 100 such as a fibroblast or an osteoblast. Three individual polypeptide chains 101$a$-$c$ are assembled intracellularly (step B) into a triple helix formation 102 also referred to as procollagen. The procollagen 102 is secreted (step C) to the extracellular environment via secretory vesicles 104. The non-helical propeptide ends 105$a$-$c$ of the procollagen molecule 102, which prevent fibril formation, are subsequently cleaved (step D) by the action of procollagen peptidase, resulting in a collagen molecule 106. The collagen molecule has a length of about 250-300 nm and a diameter of about 1.5 nm.

In the extracellular environment, the collagen molecules 106 self-assemble, both laterally and end-to-end, to form a fibril 107 (step E). Each fibril has a length of 5-200 µm and a diameter of 10-300 nm and consists of collagen molecules 106 closely packed in a quasi-hexagonal lattice. In the fibril 107, adjacent molecules 106 point in the same direction and are substantially parallel with the fibril axis, and the collagen molecules are staggered regularly within the fibril 107. A plurality of collagen fibrils 107 are subsequently assembled (step F) to form a collagen fiber. A collagen fiber may have a diameter of 0.5-3 µm, and in cross-section may have about 270 collagen molecules.

FIG. 2 further illustrates the hierarchical structure of a natural collagen fiber 108. Collagen provides structural support to the extracellular matrix, and also affects cell development by binding to transmembrane receptors of cells. The $\alpha 2\beta 1$ integrin is a receptor with affinity for the hexapeptide GFOGER sequence of triple-helical collagen type I. Integrin signaling is bidirectional, and integrin binding to extracellular ligands such as collagen can trigger a series of complex events within the cell, referred to as outside-in signaling, which ultimately may affect cell viability and spreading, migration, proliferation and/or differentiation. During integrin activation, e.g. by binding of collagen, conformational changes occur not only in the extracellular region of the integrin but also in the cytoplasmic part by separation of the cytoplasmic tails of the $\alpha$ and $\beta$ subunits. The separated tails allow interaction with intracellular signaling molecules and subsequent intracellular signal transduction.

As used herein, "collagen" when used alone or in expressions like "collagen type I" refers to any structural composition of one or more collagen molecules, for example a single collagen molecule, a collagen fibril or a collagen fiber, or a plurality of such entities.

As used herein "collagen fibril" specifically refers to a plurality of collagen molecules assembled to form an individual elongated fibril having a diameter of 10-300 nm and a length of 5-200 µm. When such fibrils are not assembled to form a collagen fiber it may be referred to as "individual collagen fibrils" or "fibrillar collagen". Collagen types that may be provided as fibrillar collagen include collagen type I, type II, type III, type V and type XI.

"Collagen fiber" as used herein, specifically refers to a bundle of collagen fibrils forming an elongated fiber having a diameter of about 0.5-300 µm. A collagen fiber or a plurality of collagen fibers does not constitute fibrillar collagen.

As used herein, "linker molecule" refers to any conventional molecule which is capable of linking an entity of interest, here collagen fibrils, to a carrier, e.g. a substrate surface. The linker may bind to the carrier and the entity of interest, respectively, by any suitable binding mechanism, which may be the same or different for the carrier and the entity of interest. The linker molecule may also be referred to simply as "linker". A single linker molecule may have multiple binding sites available for the collagen fibrils to bind. The linker is capable of binding to at least one collagen fibril at an end of the fibril.

In the present invention, an individual collagen fibril may bind to at least one linker molecule. Depending on the type of linker used, more than one collagen fibril may bind to a single linker molecule, and a single collagen fibril may bind to more than one linker molecule. It is believed that this may be due to the end of the fibril being slightly disentangled or unraveled, exposing the ends of individual collagen molecules, which thus may provide multiple binding sites for the linker(s).

When a collagen fibril is attached at one end to a linker molecule, the end of the fibril that is not bound to the linker molecule may be referred to as the distal end of the fibril. When the distal end of the fibril is not bound to another entity, such as another fibril, it may be referred to as a "free end".

A collagen fibril that is directly bound to the linker may be referred to as "primary fibril", whereas a fibril that is attached to the distal end of the primary fibril may be referred to as a "secondary fibril".

Figure 3A:
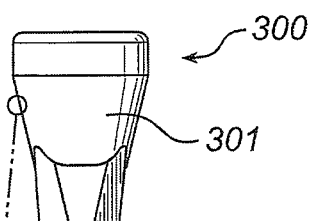
FIG. 3a-c schematically illustrate a biocompatible article having a surface comprising collagen fibrils attached thereto according to embodiments of the invention.

FIG. 3a illustrates a biocompatible article according to an embodiment of the invention. The biocompatible component of this embodiment is a dental abutment 300 which is to be attached to a dental fixture (not shown) and is adapted to receive a restoration tooth (not shown). The abutment 300 has a surface 301 intended for contact with the gingival tissue of the patient after implantation.

Figure 3B:
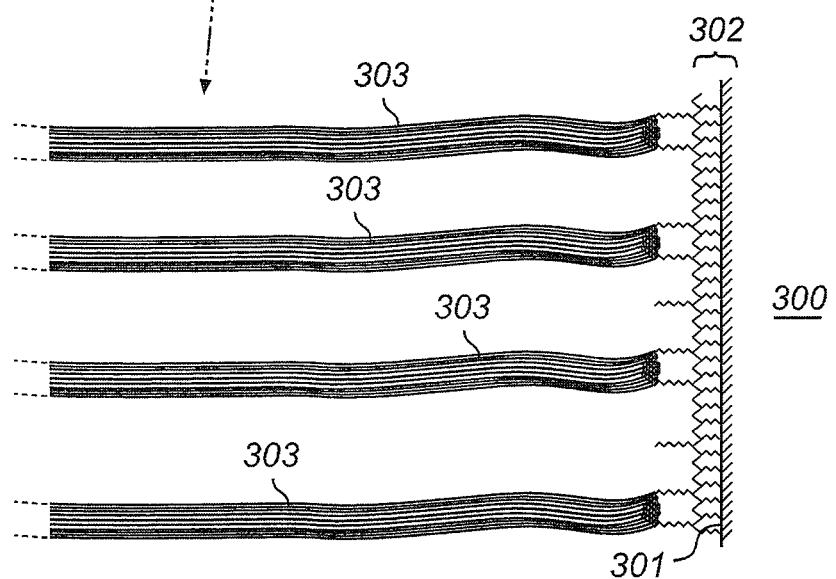

FIG. 3b shows in high magnification a schematic cross-sectional side view of a portion of the surface 301 of the article 300. Onto the surface 301, a linker molecule 302, here poly-L-lysine (PLL), has been attached. Further, collagen fibrils 303 are attached to the linker molecules. The collagen fibrils 303 are attached to the linker molecule at one end of the fibril, and the individual fibrils are substantially straight and oriented generally outwards from the surface 301 of the biocompatible article. All, or at least most, of the collagen fibrils 303 are oriented generally in the same direction, outwards from the surface. This orientation of the collagen fibrils is in contrast to known collagen surface coatings for biocompatible articles and implants. Typically the surface may be covered with a layer of linker molecules.

The collagen fibrils of the present invention are each composed of a plurality of collagen molecules assembled into a fibril 303 similar to fibril 107 of FIG. 1. Importantly, the collagen fibrils 303 are present as individual fibrils, and do not form part of a collagen fiber. The fibrils typically have a length in the range of about 20 to 200 μm, and a diameter in the range of 100 to 400 nm, preferably 50 to 150 nm. Typically each collagen fibril is attached via at least one linker molecule to the surface of the biocompatible component.

Figure 3C:
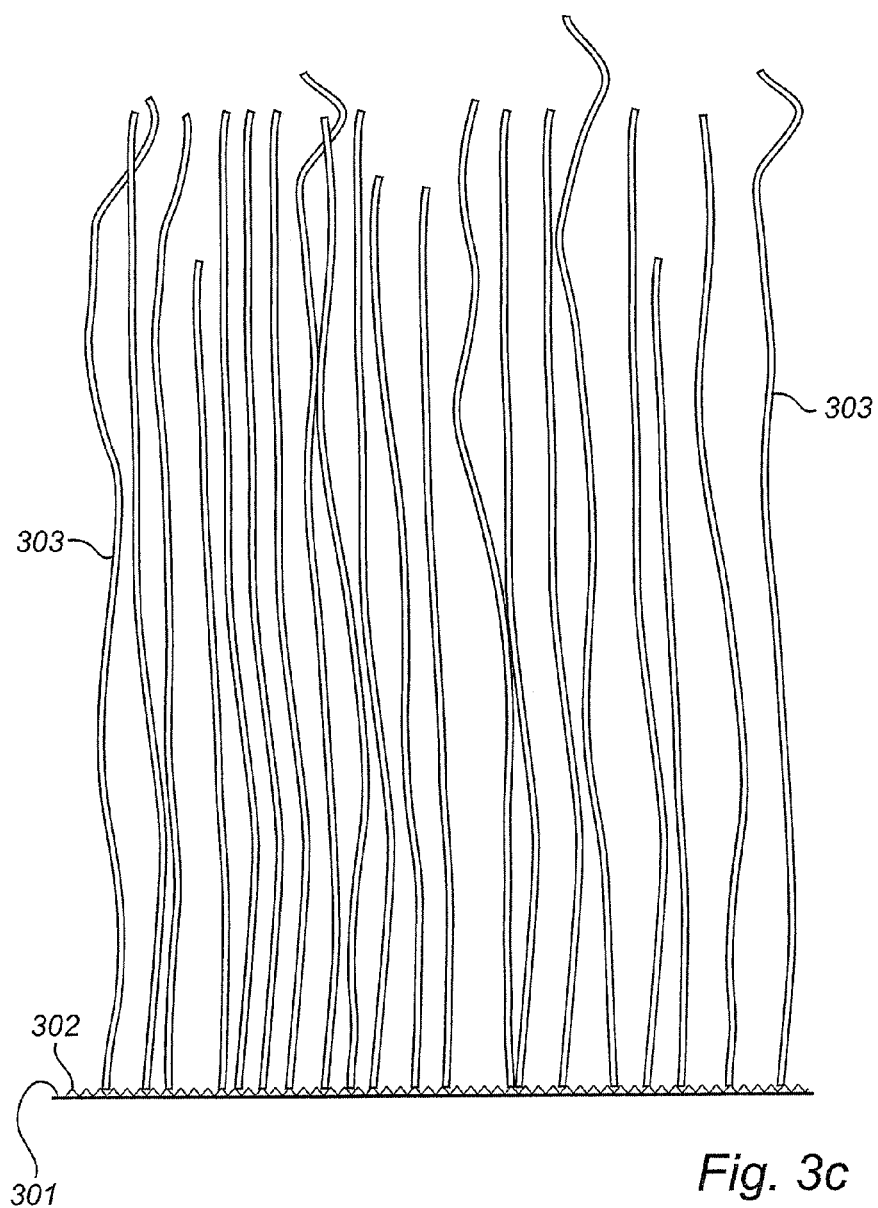

FIG. 3c also illustrates the surface 301 having the fibrils 303 attached thereto, with a slightly lower degree of magnification. As can be seen in this figure, the collagen fibrils are oriented substantially vertical to the surface 301 for a major portion of their length. In this context, "substantially vertical" means at most 10° deviation from the surface normal. As illustrated in FIG. 3c, at the distal end of the fibril 303, counted from the implant surface, the collagen fibrils are more bending. It is believed that a high density of collagen fibrils could possibly contribute to their relatively straight, vertical orientation vis-à-vis the surface 301. It is also believed that the free ends of the fibrils may be more free to move and bend, since not all fibrils have the exact same length, but some may be shorter and thus leave room for the free ends of longer fibrils to bend and coil.

Figure 3D:
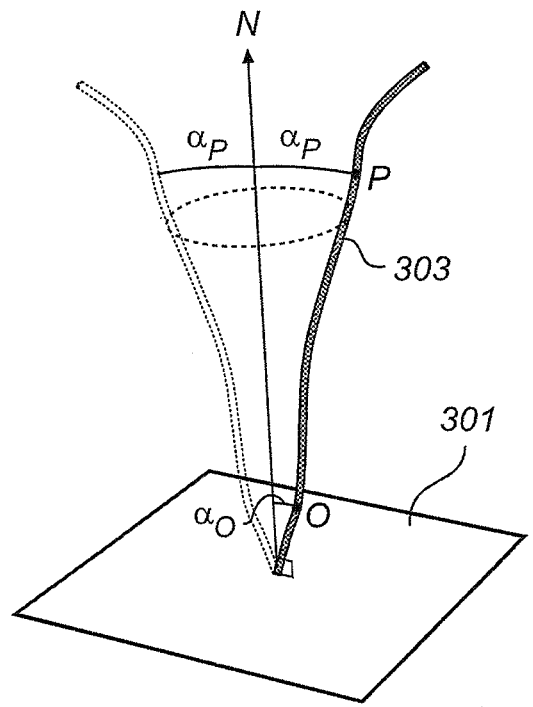
FIG. 3d schematically shows in a perspective view an example of a collagen fibril on a surface, illustrating the surface normal N, the point P, the angle $\alpha_P$, the point O, and the angle $\alpha_O$.

FIG. 3d schematically illustrates a single collagen fibril attached to the surface 301, marking the angle $\alpha_P$ between the surface normal N and the fibril at a point P somewhere along the fibril. Similarly, an angle $\alpha_O$ is defined between the surface normal N and the fibril at a point O, located between the proximal end of the fibril (i.e. the end attached to the surface) and the point P. The values of angles $\alpha_P$ and $\alpha_O$ are always defined as positive numbers.

Figure 3E:
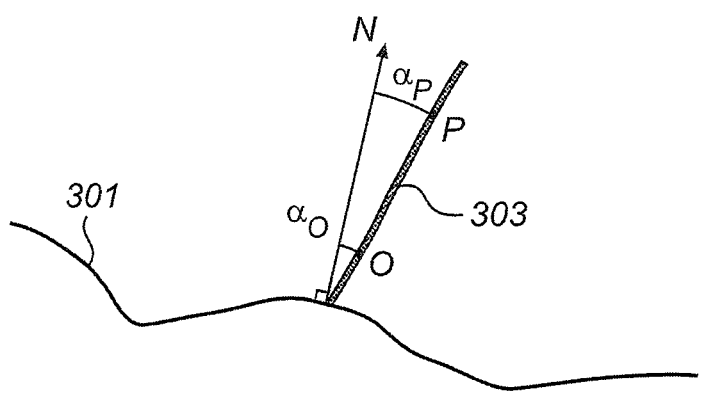
FIG. 3e illustrates a fibril, the surface normal, the points P and O and the angles $\alpha_P$ and $\alpha_O$ in a cross-sectional view.

FIG. 3e schematically illustrates a fibril, the surface normal, the points P and O and the angles $\alpha_P$ and $\alpha_O$ in a cross-sectional view of the surface.

The substantially vertical orientation of the individual collagen fibrils can be achieved by a method as described herein, which allows the individual collagen fibrils to attach to linker molecules at an end of the fibril.

The particular fibril orientation provided by the present invention is in contrast to known collagen coatings, which usually result in collagen fibrils or fibers lying more flat on the surface. It is believed that the present structure of collagen fibrils attached (via the linker) to the surface of the biocompatible article resembles the natural structure of collagen fibrils in vivo, possibly as produced by cells present at a site of an implant following implantation during tissue regeneration and/or tissue remodeling. Thus, the invention may stimulate or enhance the natural response of a cell to tissue injury and promote the formation of new tissue.

Furthermore, it is believed that when the biocompatible article according to the invention is contacted with a biological environment, e.g. upon implantation into the body of a human or a mammalian animal, cells such as fibroblasts or osteoblasts will be attracted to the implant surface, because the surface comprising collagen fibrils mimics the structure of a surface on which the natural process of tissue regeneration has already been initiated. Cells attracted to the surface of the article can attach to the coating of collagen fibrils, proliferate and start to produce native collagen while simultaneously degrading the collagen fibrils originally attached to the surface. Thus, it is believed that the present invention may promote tissue regeneration by attracting cells to the surface of the biocompatible article and/or initiate or enhance early production of native collagen and other ECM components necessary for creating a strong interface between biological tissue and an implant.

The linker used in the present invention serves to attach the collagen fibrils to the surface with the desired orientation. The linker may be any biocompatible molecule conventionally used as a linker in biochemical or biomedical applications to attach a molecule or cell to a substrate surface. Examples of linker molecules that are contemplated for use in the present invention include poly-L-lysine, poly-D-lysine, and covalent carbodiimide coupling. In addition to being biocompatible, the linker should be capable of binding to the end of a collagen fibril.

In embodiments of the invention, the linker is poly-L-lysine (PLL). Since PLL has cationic side chains, it readily binds to negatively charged entities present on a surface or another molecule, through electrostatic interactions. It is believed that when PLL is used as the linker molecule in embodiments of the present invention, it may electrostatically bind negatively charged C-terminal ends of the α-chains of collagen molecules that are present and available for physical and electrostatic interactions at the end of a collagen fibril. Thus, a PLL molecule may bind a collagen fibril at one end of the fibril.

As an alternative to PLL, the linker molecules may be a covalently surface-attached molecule, e.g. a carboxyl reactive resin which may form a covalent bond to the C-terminus of a peptide, such as the polypeptides of a collagen molecule.

The PLL used in embodiments of the invention typically has a molecular weight (MW) in the range of 70,000 to 150,000 g/mol, which represents a polymer consisting of about 480-1000 lysine repeating units. Assuming that every second repeating unit provides a positive charge that may provide a binding site for binding a negative charge of a collagen fibril, each PLL molecule would provide about 240-500 possible binding sites for collagen fibrils. A single collagen fibril may bind simultaneously to multiple binding sites of a linker molecule, as outlined above.

In embodiments of the invention, not all binding sites of the linker molecule that are available for binding to collagen fibrils are actually bound to a fibril. Thus, there may be linker molecules present on the surface 301, which are attached to the surface 301 but not to saturated with collagen fibrils. Such linker molecules may, particularly in the case of PLL, to some extent contribute to attracting biomolecules and cells to the surface after implantation. However, too much free PLL on a surface may have a cytotoxic effect.

The biocompatible article typically has a density of collagen fibrils in the range of from 1 to 50 fibrils per $\mu m^2$, for example 2 to 50, 5 to 50 or 10 to 50 fibrils/$\mu m^2$. The collagen fibril density may be substantially constant within a distance of at least 5 μm, and typically at least 20 μm, and possibly up to 100 μm or up to 200 μm, from the surface of the article, which may correspond to the length of most of the collagen fibrils. The present inventors have found that at larger distances from the surface the orientation and/or density of collagen fibrils may differ from the situation closer to the surface, due to bending or coiling of the fibrils and/or fibril-to-fibril attachment. For example, it is believed that secondary collagen fibrils may attach end-to-end to the distal ends of the primary fibrils attached via the linker molecules.

The collagen used in the present invention may be of human origin. Human collagen type I may be preferred for implants intended for implantation into the soft tissue or bone tissue of a human patient, since it would avoid or reduce problems related to an immunogenic response of the patient. However, collagen is highly similar between species, and less immunogenic than many other proteins used in implantable devices, and in some instances it may be advantageous to use collagen of e.g. bovine or equine origin. Another possibility is to use recombinant collagen I, which may offer the advantage of being less immunogenic to human patients than bovine or equine collagen and less expensive than human collagen.

For implants intended for implantation into cartilage tissue, the collagen of the present invention may be collagen type II and/or collagen type III, which also form collagen fibrils.

The surface of the biocompatible article according to embodiments of the invention may be moderately hydrophilic. By "moderately hydrophilic" is meant that the hydrophilicity (wettability) may be higher compared to a surface having a conventional collagen coating, yet not as high as that of an uncoated surface. For example, the water contact angle of the biocompatible article may be in the range of 20° to 40°, and typically 25° to 35°.

In embodiments of the invention, the biocompatible implant may further comprise one or more additional biologically active agents. It is contemplated that the collagen fibrils may be used as a carrier or substrate for such agents. For example, an antibacterial substance such as an antibacterial peptide may be attached to the collagen fibrils. Alternatively, a biologically active agent may comprise an antifungal or antibacterial agent or an antibiotic. Alternatively, the biologically active agent may comprise a cell growth or cell activity promoting substance such as ECM components, e.g. vitronectin, laminin-5 or hyaluronic acid, growth factors, e.g. VEGF, IGF, TGF or FGF, or bone growth enhancing agents, e.g. hydroxyapatite, bone morphogenic proteins (e.g. BMP-2, BMP-6), bisphosphonates, lithium or strontium.

The biocompatible article may be made of any suitable biocompatible material, e.g. materials used for implantable devices. Typically the biocompatible article comprises a body having said surface. The body may for example be made of a biocompatible metal or metal alloy, including one or more materials selected from the group consisting of titanium, zirconium, hafnium, vanadium, niobium, tantalum, cobalt and iridium, and alloys thereof. Alternatively, the body of the biocompatible article may be made of a ceramic, such as zirconia, titania, shape memory metal ceramics and combinations thereof. In embodiments where the biocompatible article is used as or forms part of a dental abutment, the body is preferably made of a ceramic material.

In contact with oxygen, the metals titanium, zirconium, hafnium, tantalum, niobium and their alloys instantaneously react to form an inert oxide. Thus, the surfaces of articles of these materials are virtually always covered with a thin oxide layer. The native oxide layer of a titanium body mainly consists of titanium(IV) dioxide ($TiO_2$) with minor amounts of $Ti_2O_3$, TiO and $Ti_3O_4$.

Thus, in embodiments where the biocompatible article comprises one or more of titanium, zirconium, hafnium, tantalum, niobium or an alloy of any one thereof, the surface of the biocompatible article (to which the collagen fibrils are attached) typically comprises a native metal oxide.

In other embodiments of the present invention, the biocompatible article, in particular the body of the biocompatible article, may be made of a biocompatible polymer, typically selected from the group consisting of polyether ether ketone (PEEK), poly methyl methacrylate (PMMA), poly lactic acid (PLLA) and polyglycolic acid (PGA) and any combinations and copolymers thereof.

The biocompatible article of the invention may be an implant, for example a dental implant, including a dental fixture, an abutment, or combinations thereof, such as a one-piece dental implant. It may also be an orthopaedic component, such as a hip joint component intended for implantation into the neck of the femur of a patient.

The surface onto which the collagen fibrils are attached may be smooth or may have an underlying roughness. In the case of metallic dental fixtures and other implants intended for contact with bone, it is generally desirable to have a small degree of surface roughness, for example an $R_a$ in the range of 0.5 to 1.5 μm. In other embodiments, for example in the case of a ceramic dental abutment, the surface of the biocompatible article may be more smooth, e.g. having an $R_a$ of less than 0.5 μm, typically less than 0.1 μm. In embodiments of the invention, a relatively smooth surface or a surface having only a fine roughness may be preferred, since it more easily allows the fibrils to be oriented in the same direction.

Figure 4:
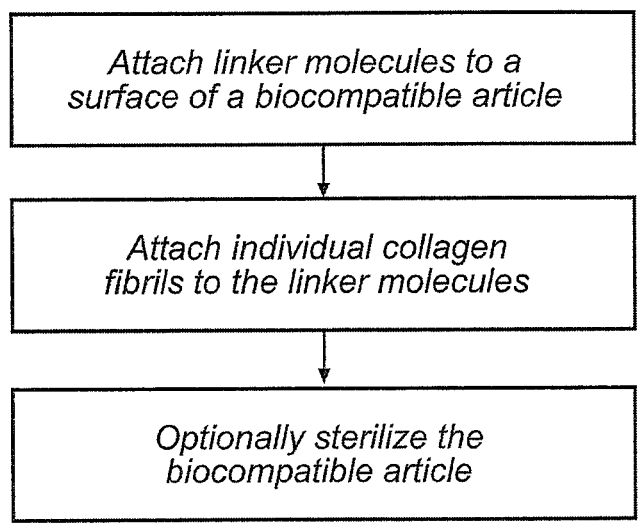
FIG. 4 is a block diagram illustrating the method according to the invention.

The biocompatible article according to the invention is produced by coating the surface of a biocompatible article, such as a conventional biocompatible article, with a collagen fibrils in such a manner that most or substantially all of the fibrils are attached to the surface of the article at one end of the fibril and oriented in a longitudinal direction substantially vertical to the surface of the article. This may be achieved by first attaching a linker molecule to the surface of the biocompatible article, and subsequently attaching the collagen fibrils to said linker molecules. These steps are schematically illustrated in FIG. 4. After attaching the collagen fibrils, the biocompatible article may optionally be subjected to a mild sterilizing treatment, before use e.g. as an implant or a part thereof.

The linker may be attached to the surface of the biocompatible article by any suitable means, including for example electrostatic interaction, hydrophobic interaction, or covalent binding. In particular, the linker molecule may be attached to the surface via electrostatic interaction. For example, on a surface having a negative electric charge, such as a titanium oxide surface of a titanium article, a positively charged linker molecule such as poly-L-lysine may be attached. If necessary, the surface of the biocompatible article may be treated or modified by known methods to obtain an electric charge.

The linker molecule may be attached to the surface of a biocompatible article, by applying a solution of the linker molecule onto the surface, preferably so as to completely cover the surface with said solution. Typically, the surface is previously washed e.g. with ethanol, and dried. The solution of linker molecule may be applied by any conventional techniques, such as spraying, pouring or dripping the solution onto the surface or immersing the surface into the solution.

In the case of poly-L-lysine, the solution applied to the surface may be a solution of PLL having a concentration may be in the range of 0.01 to 1 mg/ml, typically about 0.2 mg/ml.

After applying the linker solution to the surface of the biocompatible article, the solvent is removed, leaving the linker molecules attached to the surface. For example, the solvent may be evaporated by treating the article at elevated temperature, e.g. in the range of 40 to 60° C., and typically about 60° C. The time required for allowing the solvent to evaporate may be in the range of 10 minutes to 2 hours, typically from 30 minutes to 1 hour.

Optionally, in embodiments of the invention, after applying the linker solution to the surface of the article, the article is incubated for a few minutes, e.g. 1-10 minutes, and the linker solution, except those linker molecules that have already bound to the surface, is subsequently washed off by rinsing with a rinsing agent e.g. sterile water, before the article is subjected to elevated temperature as described above. After evaporation or the solvent or the rinsing agent, the surface having attached linker molecules is optionally washed, e.g. with sterile water and dried or allowed to dry.

The collagen fibrils may be attached to the linker molecules by applying a solution comprising collagen fibrils to the surface having the linker molecules attached thereto. The solution comprising collagen fibrils may be applied to the surface by any conventional technique that leaves at least a thin film of solution covering the surface to be coated with collagen fibrils. Such methods include spraying, pouring and dripping the solution onto the surface, and immersing the surface into the solution.

The solution comprising collagen fibrils may be an aqueous solution of collagen I fibrils at a concentration in the range of from 0.1 to 10 mg/ml, typically from 0.5 to 5 mg/ml, and preferably about 1 mg/ml.

The collagen fibrils of said solution are typically individual collagen fibrils having a length of 20-200 μm and a diameter of 50-150 nm. It is contemplated that a gel or gel-like solution of collagen fibrils may also be used.

After applying a thin film of collagen solution to the surface, the biocompatible article is allowed to incubate for a time period of at least 10 minutes, typically at least 30 minutes, for example about 45 minutes, and up to several hours, typically up to 1 hour. During the incubation, the solvent of the collagen solution should preferably not completely evaporate to leave the surface dry, but there should preferably still be solution present on the surface at the end of the incubation period. Incubation may be carried out at a temperature of 40° C. or less, typically in the range of 4 to 40° C., for example at room temperature (15-25° C.). At higher temperature than about 40° C., the collagen fibrils may start to denature and the desirable fibril orientation might not be obtained.

In embodiments of the invention, the biocompatible article is incubated in a humid chamber. Incubating the article in a humid atmosphere is advantageous because it ensures that the solvent does not evaporate too fast. A humid chamber as used in embodiments of the invention typically means a closed chamber in which the component is placed, and in which is also present a pool of sterile water or a tissue soaked with sterile water. In an industrial setting the humid chamber may be a controlled chamber with 75-100% humidity. However, it should be noted that a humid chamber is not necessary, and too fast drying of the applied solution may be avoided also at ambient humidity.

After incubation (evaporation of the solvent), the surface is typically washed, e.g. in sterile water or a suitable buffer solution, to remove remaining solution, and may optionally be subjected to a suitable sterilizing treatment, e.g. UV or gamma irradiation or chemical sterilization using ethylene oxide gas. The sterilizing treatment must not destroy the collagen fibrils, and therefore heat sterilization is not suitable.

It is envisaged that further modifications could be made to the collagen fibril coating obtained by the method according to the invention. For example, a bioactive substance as described above could be applied to the collagen fibril coating. Additionally of alternatively, the collagen fibrils could be cross-linked after being attached to the surface, e.g. in order to reduce the rate of fibril degradation in vivo after implantation of the biocompatible article.

EXAMPLE 1

Sample Preparation and Characterization 1.1 Surface Preparation

Commercial pure titanium grade 4 coins with a maximum average roughness $R_a$ of 0.8 μm were cleaned and chemically processed according to a protocol used for commercial dental implants. All coins were rinsed with 97% ethanol and air-dried at room temperature. Coins intended as reference ("Ti") were processed no further.

Comparative ("Ti-PLL") and test ("Ti-PLL-Col") coins were coated with PLL by applying 150 μl of 0.2 mg/ml poly L-lysine hydrobromide (PLL, 70,000-150,000 g/mol) (obtained from Sigma Aldrich, USA) in MilliQ-water (Millipore, USA) on the surface of the coins, followed by two hours incubation at 60° C., rinsing twice in MilliQ-water and air-drying in room temperature. The comparative ("Ti-PLL") coins were processed no further.

After coating with PLL, the test coins ("Ti-PLL-Col") coins were coated with fibrillar collagen. 150 μl of 0.1 mg/ml equine fibrillar collagen type I solution (Chrono-Log Corporation, USA) was applied to the surface of each test coin by pipette, leaving a thin layer of fluid on the surface. The test coins were then incubated at room temperature for 45 minutes prior washing with phosphate buffered saline (PBS) solution.

Finally, second comparative coins ("Ti-Col") were subjected only to collagen coating as described above without any intermediate coating with PLL (i.e., no linker).

All coins were placed in 24-well plates (TPP, Switzerland), encased in autoclave bags, and sterilized by electron beam sterilization with a minimum acquired dose of 25 kGy. The 24-well plates containing the samples were then stored at 4° C. until use.

1.2 Evaluation of Fibril Orientation

In order to verify the orientation of the fibrils attached to the test surface (Ti-PLL-Col), collagen-coated surfaces prepared as described above, except that 1 mg/ml collagen fibril solution was used instead of 0.1 mg/ml, were embedded in resin, the coin was removed, and ultrathin sections were examined using transmission electron microscopy (TEM) according to the following description:

The Ti-PLL-Col specimens were immersed in 1.5% paraformaldehyde and 1.5% glutaraldehyde in 0.1 M sodium-phosphate buffer pH 7.2 for 1 h at room temperature, and then overnight at 4° C. The specimens were washed in the fixation buffer and then postfixed for 1 h at room temperature in 1% osmium tetraoxide in 0.1 M sodium-phosphate buffer, subsequently dehydrated in a graded series of ethanol, and then embedded in Epon 812 resin using acetone as an intermediate solvent. The titanium coins were removed from the respective resin portion and the specimens were cut into ultrathin sections (thickness of 50-70 nm) with a diamond knife on an LKB ultramicrotome. The sections were stained with uranyl acetate and lead citrate. The stained sections were observed in a JEOL JEM 1230 electron microscope operated at 80 kV accelerating voltage, and images were recorded with a Gatan Multiscan 791 CCD camera.

Figure 5A:
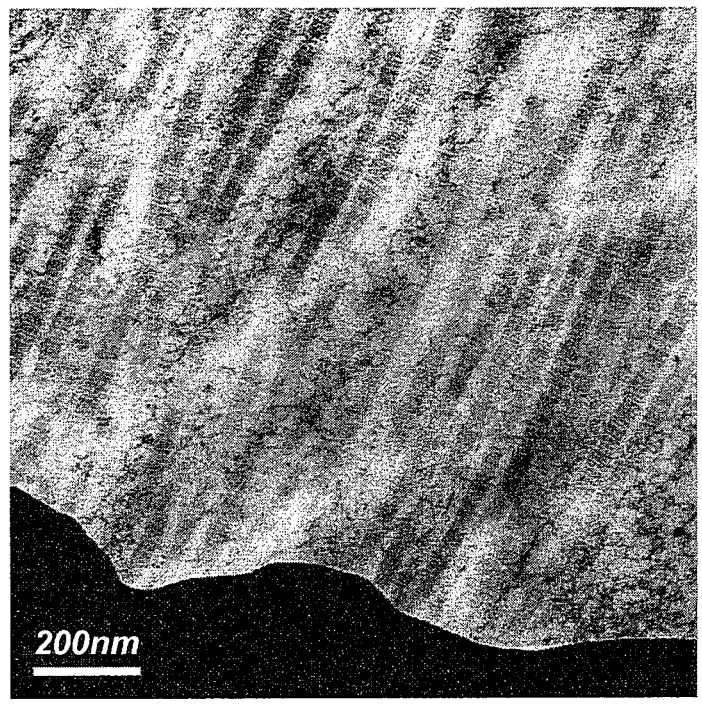
FIG. 5a-c are transmission electron microscopy images of ultrathin sections showing the orientation of collagen fibrils on surfaces according to embodiments of the invention.
Figure 5B:
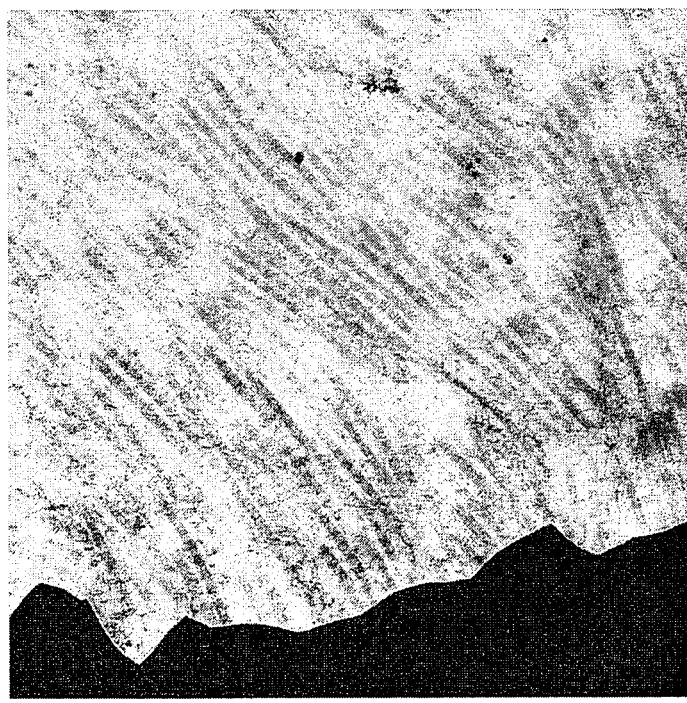

The images are shown in FIG. 5a-b. The black regions correspond to the removed titanium substrates. As can be seen, the fibrils are substantially straight and oriented outwards from the underlying surface. The scale bar of FIG. 5a represents 200 nm.

Figure 5C:
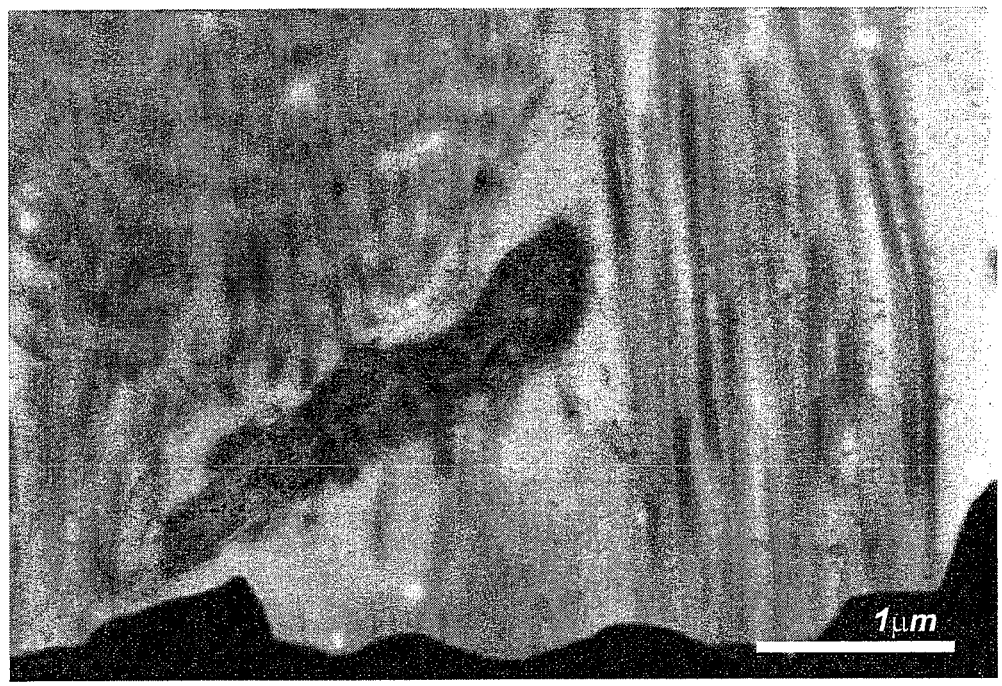

Furthermore, samples prepared using 0.1 mg/ml collagen solution as described in section 1.1 above were used for cell proliferation study, see item 2.4 below. After 3 days adhesion time, a sample was prepared for and analyzed by TEM as described previously in this section, The resulting image is shown in FIG. 5c (scale bar 1 μm). As can be seen, the collagen fibrils are oriented very much similarly to the FIGS. 5a-b, and the fibril density is comparable. A fibroblast is also seen, spreading among the fibrils. It is possible that the fibroblast has already started do degrade the collagen fibrils attached to the surface and to produce its own collagen.

1.3 Contact Angle Measurement

Figure 6A:
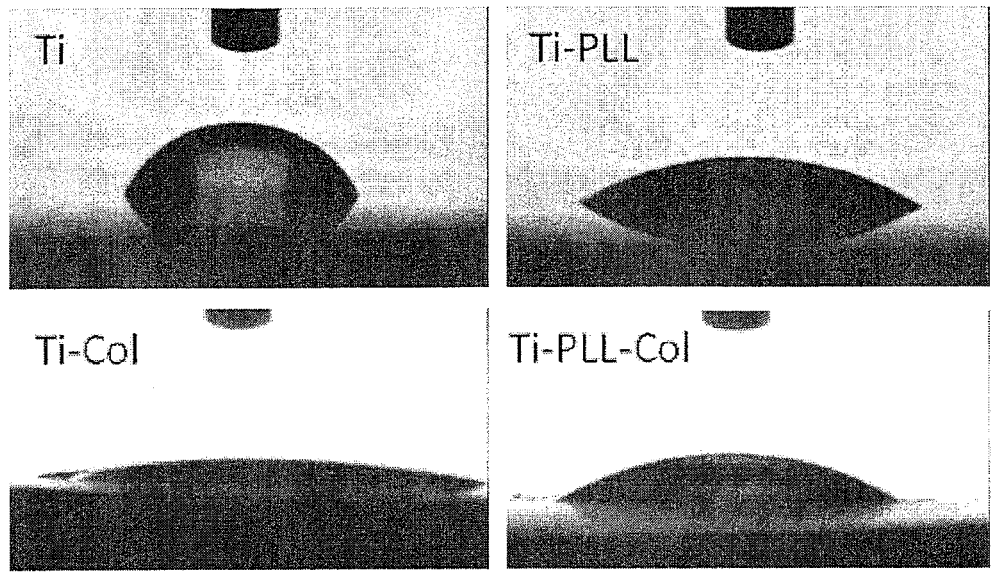
FIG. 6a and b show the water contact angle of different surfaces.
Figure 6B:
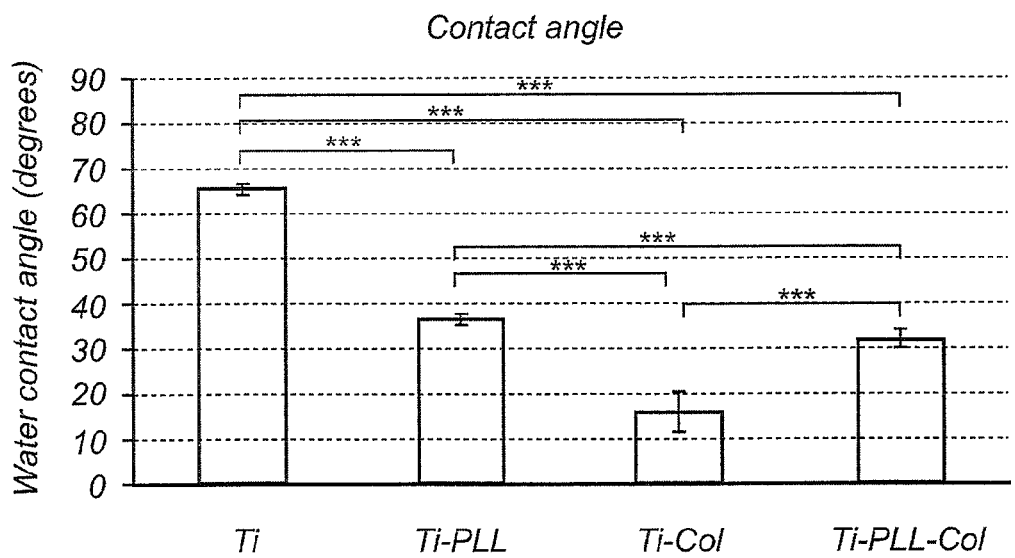

Water contact angle measurements were performed at room temperature on three samples from each the four different groups of coins ("Ti", "Ti-PLL", "Ti-PLL-Col" and "Ti-Col", respectively) by using a drop shape analysis system (DSA 100) (Krüss, Germany). The water contact angle was measured by applying a 1 μl of MilliQ water (, Millipore, USA) droplet on the sample surface. By immediately photographing the droplet and using the software DSA (KrUss, Germany) the water contact angle could be calculated. Three droplets were analyzed on each sample, i.e. nine measurements per group. The results are shown in FIG. 6a (photographs) and FIG. 6b (contact angle calculations). As can be seen, Ti had the highest water contact angle, followed by Ti-PLL, Ti-PLL-Col and Ti-Col. Error bars represent one standard deviation, ***$P<0.001$.

Interestingly, Ti-PLL and Ti-PLL-Col had similar wettability whereas Ti-Col had a significantly higher wettability. These differences in surface properties will most likely affect the biological response in terms of protein adsorption and cell adhesion. A study using surfaces with different water contact angles has shown that increasing wettability decreased albumin adsorption whereas fibronectin adsorption increased (Hao L and Lawrence J, *J Mater Sci Mater Med*, 2007, 18(5), 807-17). Thus, surface wettability may not only influence the amount of adsorbed proteins but also the type of protein adsorbed.

EXAMPLE 2

Cell Compatibility of Surfaces 2.1 Cell Culture

Human dermal fibroblasts isolated from chronic dermatitis (Hs 483.T (ATCC CRL-7814), LGC Promochem, Sweden), previously passaged four times, were thawed and seeded in a 80 cm² culture T-flask (Thermo Scientific nunc, USA) with 10 ml of complete growth medium consisting of D-MEM with 100 mM sodium pyruvate and without L-glutamine (PAA Laboratories, Austria), supplemented with 10% fetal bovine serum (FBS) (PAA Laboratories, Austria) and 2 mM L-glutamine (Invitrogen, USA). The medium was changed every third or fourth day and the cells were passaged twice a week. Cells were harvested by trypsinization with trypsin/EDTA (PAA Laboratories, Austria), mixed with 2 ml of FBS and 2 ml of complete growth medium and added with a splitting ratio of 1:2 to 1:3 to a new T-flask containing 10 ml of complete growth medium. Passage numbers represent total passages, thus the first passage in this study is denoted as number five since the cells had previously been passaged four times.

2.2 Immunocytochemistry and Fluorescence Microscopy

Samples were washed with PBS prior to incubation in 4% formaldehyde (Scharlau, Spain) in PBS for 20 minutes at 4° C., followed by three times washing in PBS. Samples were stored in PBS until immunocyto-chemistry staining. Prior to staining, the cells were permeabilized with 0.1% triton X-100 (Sigma Aldrich, USA) in PBS for 10 minutes. For visualization of cell nucleus and cytoskeleton, the cells were in darkness subjected to 300 nM 4',6-diamidino-2-phenylindole (DAPI) (Invitrogen, USA) in PBS, Alexa Fluor 555 conjugated phalloidin (Invitrogen, USA) 1:50 and 0.1% Triton X-100 in PBS for 20 minutes at room temperature. Cells were then washed three times with PBS for five minutes each and stored in darkness in PBS until analysis. Cells to be counterstained for adhesion points or active beta-1 integrin were subjected to blocking solution containing 5% skimmed milk powder (Scharlau, Spain) and 0.1% triton X-100 in PBS for one hour at room temperature to prevent unspecific binding of antibodies. Next, the cells were incubated with primary antibody, monoclonal mouse anti-human vinculin (Sigma Aldrich, USA) 1:400 for visualization of adhesion points or monoclonal mouse anti-human active beta-1 integrin (Abcam, UK) 1:400 dissolved in PBS containing 1% skimmed milk and 0.1% triton X-100, for one hour at room temperature. After washing the cells three times with PBS for five minutes each the cells were subjected to secondary antibody, goat anti-mouse conjugated with Alexa Fluor 488 (Invitrogen, USA) 1:1000 dissolved in PBS containing 1% skimmed milk and 0.1% triton X-100. Lastly, the cells were washed three times in PBS for five minutes and subjected to a staining solution containing DAPI and phalloidin as described above. All reagents (antibodies, blocking solutions etc.) in respective concentration were added to the samples as a 30 μl droplet. A small piece of parafilm was then placed on the sample, resulting in reagent spreading over the surface as well as protecting against evaporation. Samples were stored in PBS in darkness until analysis using fluorescence microscopy.

Fluorescence microscopy was performed with an epifluorescence microscope (Axioplan 2, Zeiss, Germany), images was captured with CCD camera (AxioCam, Zeiss, Germany). Two different objectives were used: Plan Neofluar 10x/0,30 and Achroplan 40x/0,80 (immersion objective). In order to image the different labels (DAPI, Alexa Fluor-555 conjugated phalloidin and Alexa Fluor-488 conjugated antibody) separately, three different filter sets were used: Filter set 1 DAPI (488001-0000, Zeiss, Jena, Germany), Filter set 20 (488020-0000, Zeiss, Germany) and Filter set 10 Alexa 488 (488010-0000, Zeiss, Germany). The contrast in the captured images was adjusted (unless stated otherwise) using the software AxioVision 4.2 (Zeiss, Germany).

2.3 Cell Attachment and Spreading

Cells (passage 3(7)) were harvested by trypsination as described above, counted in a hemocytometer using trypan blue to identify amount of dead cells, and finally diluted in complete growth medium to a final cell concentration of 16700 alive cells/ml. 300 μl of cell solution was added by droplet seeding to each coin followed by incubation at 37° C. for up to 180 minutes. After 30 minutes 700 μl of complete growth medium was added to the samples with incubation times of 60 and 180 minutes. After 15, 30, 60 and 180 minutes, respectively, the medium was removed and the cells were gently rinsed with PBS prior addition of 4% formaldehyde in PBS and incubated at 4° C. for 20 minutes. Finally, cells were rinsed 3 times in PBS and stored in 3 ml of PBS until fluorescent staining with DAPI and cell number quantification. 17 photographs of each sample at specific positions were captured at 10× magnification. Images were thresholded in ImageJ and nuclei were counted using the plugin "nucleus counter".

For evaluation of cell area and cell shape, the actin cytoskeleton and focal adhesions were stained, according to the description above. 35-45 images per group were captured at 40× magnification, the contrast in the images was enhanced prior threshold in ImageJ and quantification of cell area and cell shape using the tool "particle analysis". Cell shape was expressed as "circularity", defined as follows:

$$\text{Circularity} = 4\pi \frac{\text{area}}{\text{perimeter}^2} = \begin{cases} 1 & \text{for perfect circle} \\ 0 & \text{for straight line} \end{cases}$$

A reduction of cell circularity can be due to protrusions of the cell membrane resulting in larger cell perimeter, since circularity is inversely proportional to the square perimeter this will result in a reduced circularity.

Figure 7:
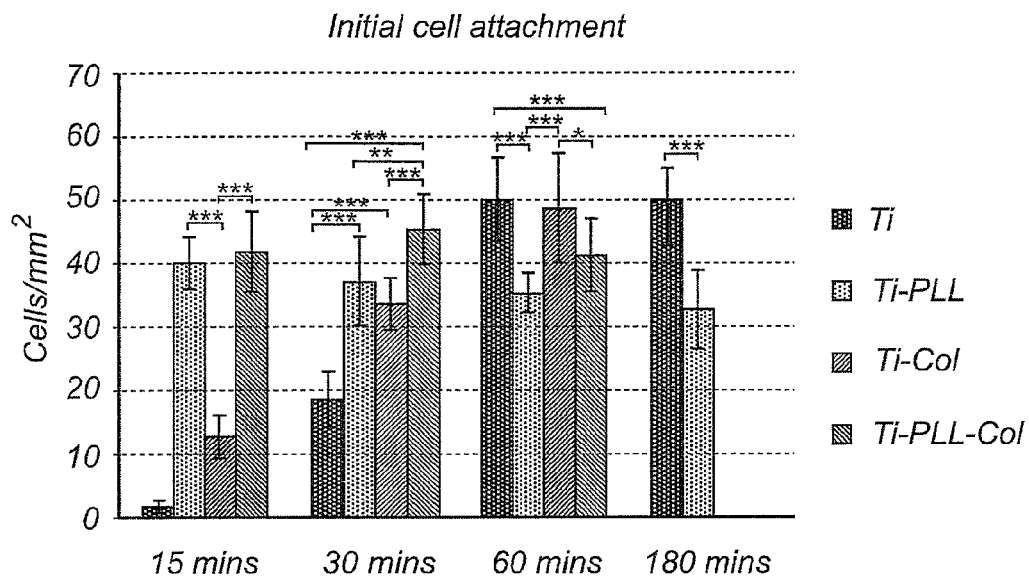
FIG. 7 is a graph showing the initial cell attachment on different surfaces.

The results for initial cell attachment to the sample surfaces are shown in FIG. 7. The Ti-Col and Ti-PLL-Col samples from 3 hour adhesion time were excluded from the analysis due to inhomogeneous cell seeding density. As can be seen in FIG. 7, all three types of surface coatings, and in particular Ti-PLL, and Ti-PLL-Col, resulted in a significantly increased amount of adherent cells compared to Ti after 15 and 30 minutes adhesion time. Error bars represent one standard deviation, *P<0.05, P<0.01, *P<0.001.

Figure 8:
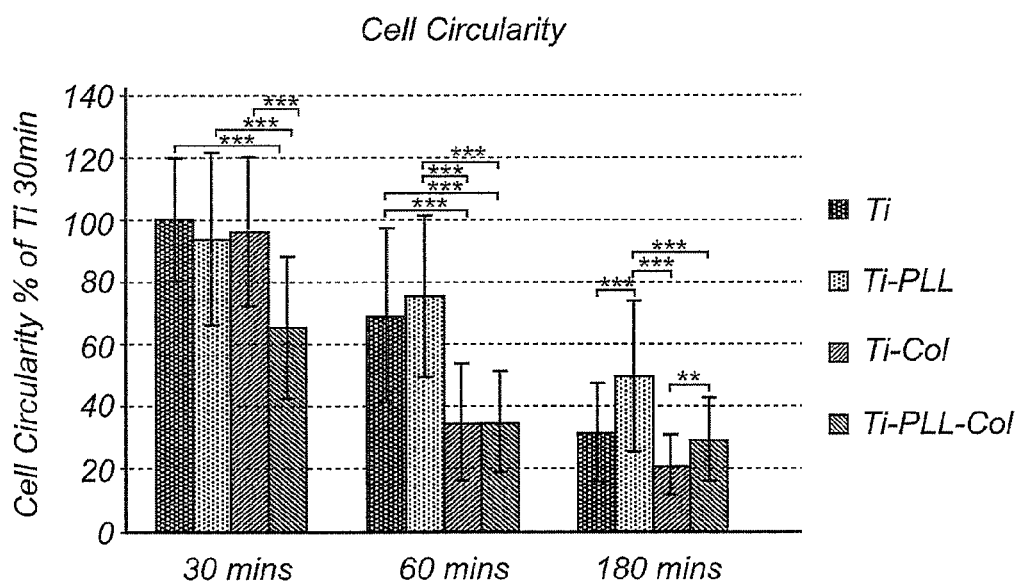
FIG. 8 is a graph showing the calculated cell circularity for cells grown on different surfaces.

The cell area quantification revealed a clear difference in cell area for Ti-PLL after 30 and 60 minutes adhesion time compared to the other groups. Ti-Col and Ti-PLL-Col did not result in any significant difference in cell area compared to Ti (not shown). However, there was a clear difference in cell shape. FIG. 8 shows the cell circularity, calculated as described above, for all four sample types. Error bars represent one standard deviation, *P<0.05, P<0.01, *P<0.001. It is seen that already after 30 minutes Ti-PLL-Col resulted in reduced cell circularity. This was apparent also after 60 minutes, where Ti-Col resulted in a similar reduced circularity as Ti-PLL-Col. The results show that the cells on Ti-PLL-Col are sensing and responding to the collagen fibrils already after 30 minutes. Further, from the fluorescence microscopy images (not shown) it was found that cells on both Ti and Ti-PLL surfaces had a circular morphology after 1 hour, whereas cells on Ti-Col and Ti-PLL-Col had a more spiky morphology (not shown). After one day the cells had a more elongated morphology compared to the earlier time points. A larger amount of thin cellular projections were also visible compared to the early time points.

2.4 Cell Proliferation

Cells (passage 1) were harvested by trypsination as described above, counted in a hemocytometer using trypan blue to identify dead cells, and finally diluted in complete growth medium to a final cell concentration of 10 000 alive cells/ml. 300 μl of cell solution (3000 cells) was added by droplet seeding to each coin. After allowing the cells adhere for 45 minutes, 700 μl of complete growth medium was added to each well before the samples were placed in the incubator at 37° C. The medium was replaced every other day. Cells were fixated after 1, 3, 6, and 10 days, respectively, stained for nuclei with DAPI, and counted in the same way as described above.

Figure 12:
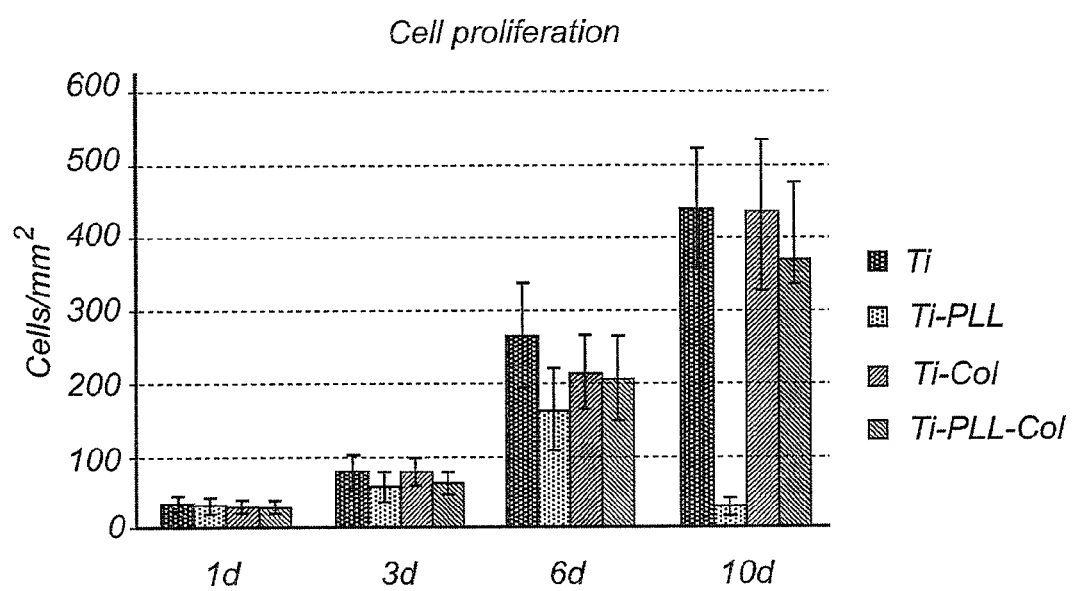
FIG. 12 is a graph showing the cell proliferation on different surfaces.

FIG. 12 shows the cell proliferation after 1, 3, 6, and 10 days, respectively. It was found that the cells were proliferating on all four types of surfaces. A very similar number of cells on the different surfaces after one day indicates on a homogenous cell seeding density. Cells on all surfaces except Ti-PLL showed very similar proliferative capacity. The cell count performed on Ti-PLL after 6 days indicated fewer viable cells than on the other surfaces and after ten days most of the cells on Ti-PLL had detached.

2.5 Cell Alignment and Elongation

The samples from the proliferation study of one day adhesion time were used to investigate the extent of cell alignment to the machining pattern of the coins as well as cell elongation. The cells on the three samples from each of the four groups were further labeled, as described above, to visualize the adhesion points and the shape of the cells. Four images of each sample were captured at 10× magnification and the contrast was enhanced to clearly make out the outline of each cell. Measurements were performed on the 10 cells located closest to the lower left corner of each image. In this way, the cells to be measured were chosen in an objective manner. A total of 100 cells per group were measured. The cell alignment to machining pattern was investigated by manually measuring the angle between the tangent to the machining pattern and a line drawn between the two mutually farthest endpoints of each cell, i.e. the cell length, as illustrated in FIG. 9a. Tangents were drawn individually for each cell at the position of the cell nucleus. The cell elongation was measured by drawing the longest possible line being perpendicular to the cell length (L), i.e. cell width (W), see FIG. 9b.

FIG. 10 shows the cell elongation after 1 day adhesion time, expressed as the ratio between cell length and width. As can be seen in this figure, cells on Ti and Ti-PLL were more elongated than cells on Ti-Col and Ti-PLL-Col. Bars represent the mean elongation of totally 100 cells from three replicates of each group. Error bars represent one standard deviation, ***P<0.001.

Figure 11:
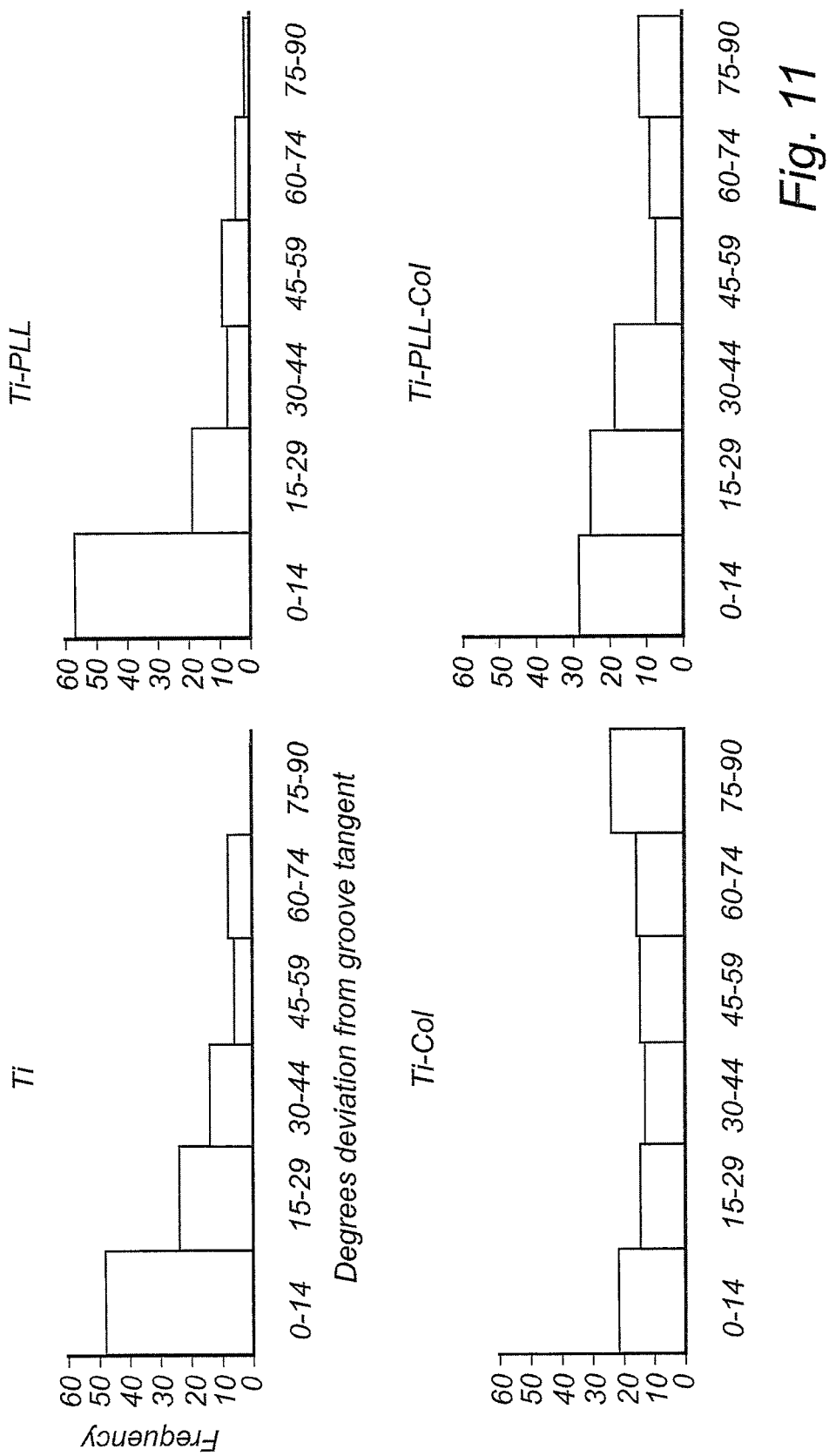
FIG. 11 present graphs showing the cell alignment to machining patterns on different surfaces.

FIG. 11 shows the extent of cell alignment to the machining grooves of the coins after 1 day adhesion time. 0° deviation corresponds to strict alignment along the machining groove, and 90° deviation corresponds to a cell orientation perpendicular to the machining grooves. The results demonstrate that the collagen-coated surfaces, Ti-Col and Ti-PLL-Col, induce more variable cell orientation compared to Ti and Ti-PLL.

2.6 Quantification of Cell Adhesion Points

Figures 13A, 13B:
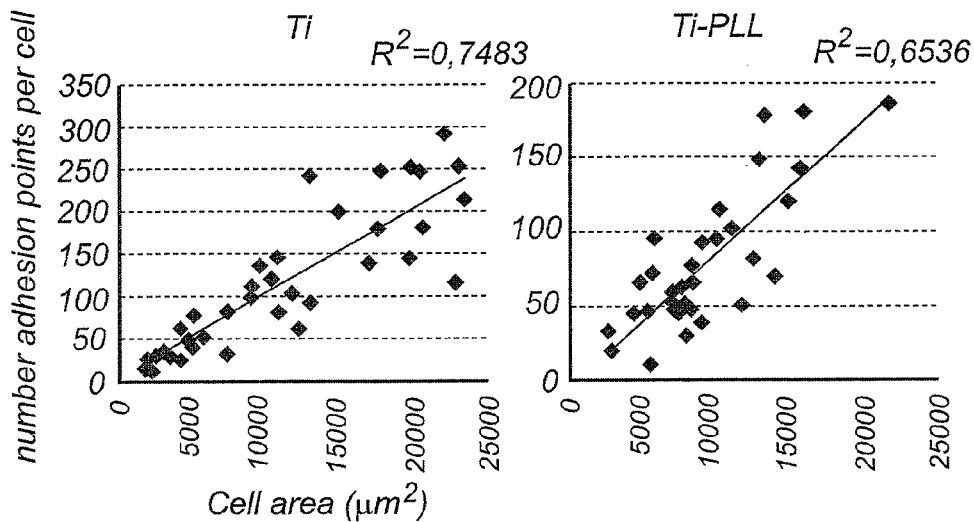
FIG. 13 shows graphs illustrating the number of adhesion points per cell on different surfaces, plotted against the cell area after three days adhesion time.
Figures 13C, 13D:
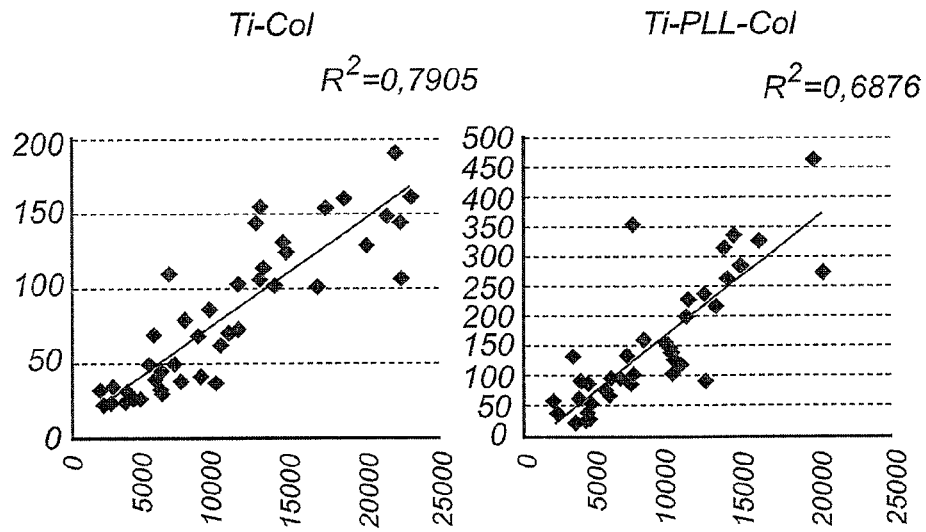

Cells from the proliferation experiment, three days adhesion time, were labeled by immunocytochemistry for adhesion points (vinculin) and actin filaments (phalloidin) as described above. Images of at least 35 cells per group at 40× magnification were captured in order to quantify adhesion points. The contrast of the adhesion points was enhanced in the software AxioVision 4.2 before quantification using ImageJ and the "analyze particle" function. All objects larger than 0.5 μm$^2$ were counted as adhesion points. The number of adhesion points per cell was correlated to the cell size. The result is presented in FIG. 13 a-d, showing the number of adhesion points per cell plotted against cell area, three days adhesion time. The adhesion points of at least 35 cells per group were quantified. A linear trend between cell area and number of adhesion points per cell is observed for all groups after three days adhesion time. As can be seen, the Ti-PLL-Col surface had a higher number of cells with at least 200 adhesion points. This may indicate that cells on the Ti-PLL-Col surface are stimulated to differentiate earlier compared to the other surfaces.

Figure 14:
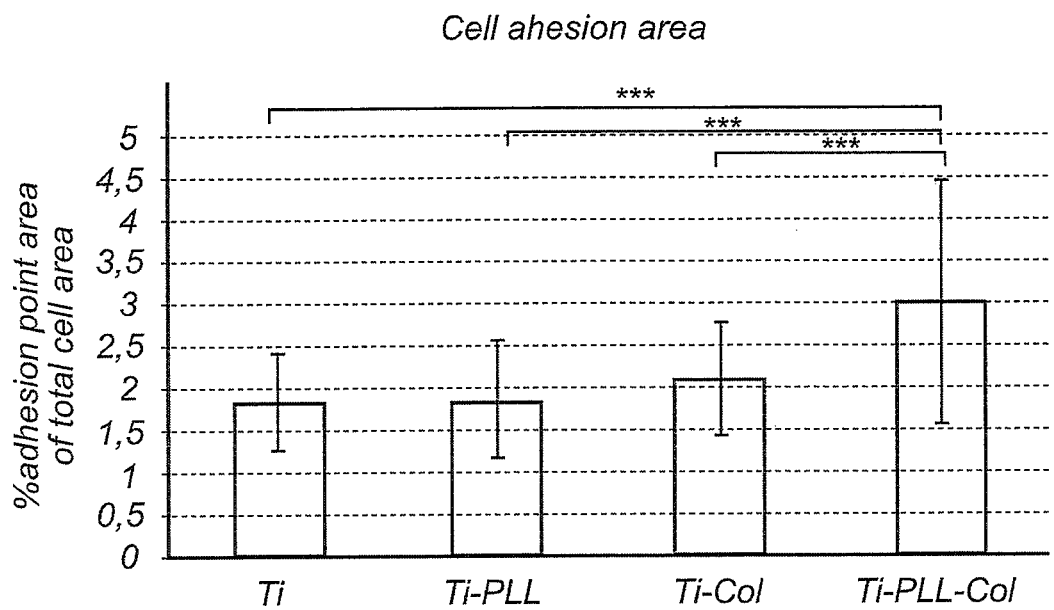
FIG. 14 is a graph showing the cell adhesion area of cells grown on different surfaces.

Next, the average cell area fraction labeled positive for vinculin was quantified for each group. It was found that cells on Ti-PLL-Col had a larger number of adhesion points per cell compared to other groups (data not shown). FIG. 14 shows the cell adhesion area, expressed as the average percentage of the total cell area labeled positive for vinculin. Error bars represent one standard deviation, *P<0.001. As shown in FIG. 14**, the average fraction of total cell area labeled positive for vinculin was higher on Ti-PLL-Col compared to the other groups. It appears that the combination of PLL and collagen is responsible for this increase in adhesive area, since this effect is not seen using PLL or collagen alone. It has been shown that there is a linear relationship between the area of adhesion points and the cellular adhesion strength to the substrate (Chimutengwende-Gordon, M., C. Pendegrass, and G. Blunn, *Biomed Mater*, 2011. 6(2): p. 025008; Balaban, N. Q., et al., Nat Cell Biol, 2001. 3(5): p. 466-72). Thus, cells on Ti-PLL-Col are probably adhering more strongly to the underlying surface.

2.7 Activation of Beta-1 Integrins

Cells (passage 5) were harvested by trypsination as described previously, counted in a hemocytometer using trypan blue to identify the amount of dead cells, and finally diluted in complete growth medium to a final cell concentration of 6000 alive cells/ml. 500 µl of cell solution (3000 cells) and 500 µl of complete growth medium was added to each coin. The cells were incubated at 37° C. for one hour, one day or three days, respectively, before fixation and immunofluorescent labeling of the cell nuclei and active beta-1 integrins. Samples for negative control were only subjected to secondary antibody, and fixated after 1 day. The actin cytoskeleton was not labeled in order to avoid any potential overlapping signal.

Cells on both Ti-Col and Ti-PLL-Col showed a clear difference in activation pattern of beta-1 integrin compared to cells on Ti and Ti-PLL. The distribution of active integrins on Ti and Ti-PLL was diffuse whereas the distribution on Ti-Col and Ti-PLL-Col was more structured; short line segments of the cells had a clearly higher activation of beta-1 integrins.

The collagen fibers were visible in the fluorescence microscope, using the filter set for DAPI. By increasing the contrast to visualize the collagen fibers and overlaying an image of the activation of beta-1 integrin, it was seen that integrins were highly activated at the positions of collagen fibers.

EXAMPLE 3

Surface Compatibility with Osteoblasts 3.1 Sample Surface Preparation

PLL+collagen fibril coated discs of commercially pure (c.p.) titanium ("PLL+Coll") were prepared as described above, Clean uncoated c.p. tianium discs were also used for comparison.

3.2 Cell Culture

Human palatal mesenchymal cells (HEPM 1486; ATCC) were cultured in Eagles Minimal Essential Media (EMEM) with Earl's Salts with 10% fetal bovine serum (FBS) and Pen/Strep antibiotics [25 mg/ml], and ascorbate [50 mg/ml], NaPyruvate [1 mM], non essential amino acids [0.1 mM], L-glutamine [2 mM], cultured with 5% $CO_2$. Cell culturing entailed isolating HEPM cells via typsin, counting (with a hemocytometer), pelleting and suspension at 50,000 cells/10 µl. 10 µl of cell suspension (Micromass approach) was plated on each test and control surface, the culture allowed to adhere for 1 hour before gentle flooding with 1 ml of EMEM+10% FBS (Stanford, Jacobson et al, 1995, Journal of Biological Chemistry 270(16):9420-9428).

For the assays, 3 discs/group/time point were used. The assays were performed through day 14 with assays performed on day 0, day 1, day 4, day 8 and day 14, respectively. The zero time point was an aliquot of the cell suspension made prior to plating. Change of media was done every four days. 100 µl of media were collected from each well of a twenty four well dish in which the discs were incubated.

Collected media were stored for proteomic assay for bone-related protein expression. Media collection for the proteomic measurement from the media was made at days 0, 1, 2, 4, 6, 8, 12.

3.3 Cell Proliferation

Cell proliferation was measured over a 14 day period using a standard MTT assay. Vybrant MTT Cell Proliferation Assay (Molecular Probes Kit V-13154) is a microplate absorbance assay, which uses the conversion of water soluble MTT (3-(4,5-dimethylthiazol-2-yl)-2,5-diphenyltetrazolium bromide) into an insoluble formazan. The formazan is then solubilized and read in a microtiter plate reader at 570 nm.

Microdots (50,000 cells/10 µl media) of HEPM cells were placed onto discs in a 24-well plate. After 1 hour (to allow cell attachment) the discs were flooded with 1 ml EMEM supplemented with ascorbate [50 mg/ml]. The media also contained 10% FBS and Pen/strep. After 24 hours the Invitrogen Vybrant MTT Cell Proliferation Assay was followed to collect samples for day 1. The samples were incubated overnight at 37° C. in SDS-HCl solution, then mixed and read at an absorbance of 570 nm. This procedure was repeated for samples at day 2, day 4, day 6, day 8 and day 14.

Figure 15:
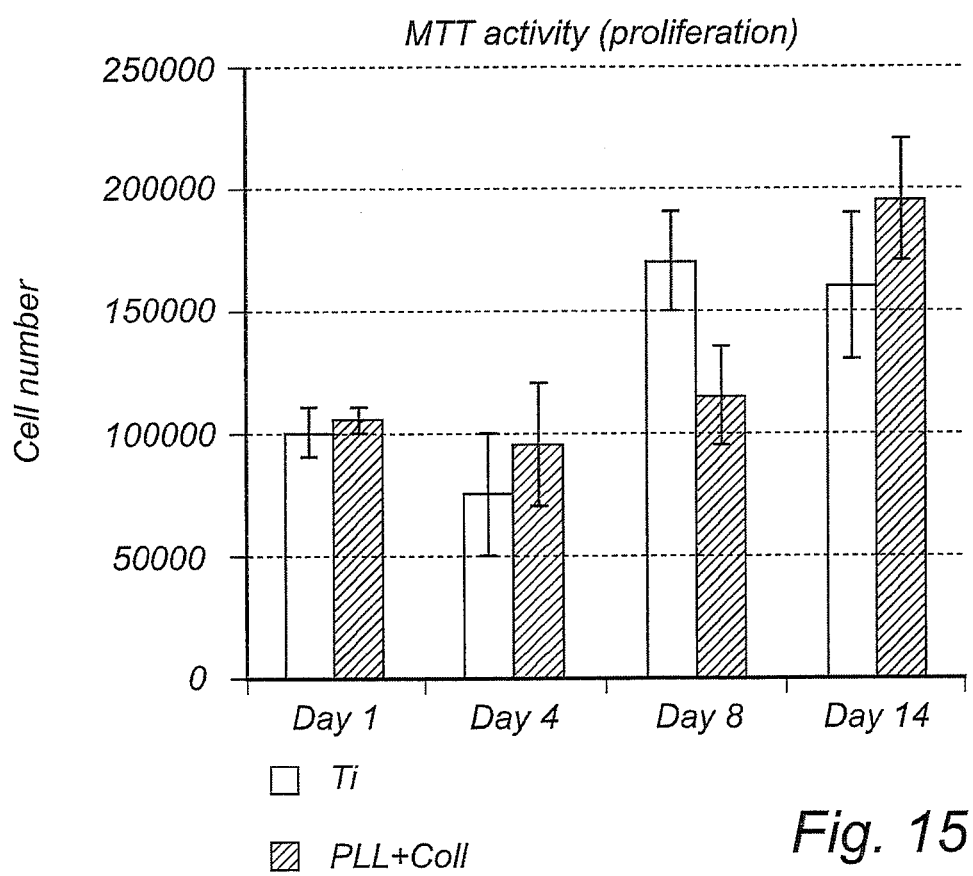
FIG. 15 is a graph showing the results of the proliferation assay.

Cell proliferation was compared to a standard curve. For statistical evaluation, two way analysis of variance (ANOVA) with Bonferroni multiple comparison evaluation was performed (Prism 5.0, GraphPad Inc.). The results of the proliferation assay, shown in FIG. 15, indicate a progressive increase in cell number on the reference surface Ti with a slight decline noted at day 14. Cells grown on the collagen fibril coated surface (PLL+Coll) had a slight delay in growth but by day 14 had the highest density (p, 0.01) compared to the Ti surface.

3.4 Cell Activity: Gene Expression Levels of Bone Related Gene Markers

Changes in osteoblast gene expression for alkaline phosphatase, cbfa1, and BMP-2 were analyzed using multiplex and real time PCR strategies at days 0, 1, 4, 8 and 14. Micromass cultures (50,000 cells/10 µl media) were plated in triplicate on plastic as a control as previously described (Schneider, Zaharias et al., 2004. Journal of Biomedical Materials research. 69A 3:462-468) After 1 h of attachment, wells were flooded with EMEM/10% FBS and 50 mg/ml ascorbate. At days 0, 1, 4, 8 and 14, total cell RNA was extracted with RNeasy Mini Kit (Qiagen), according to the manufacturer's instructions. Cells were then homogenized (QIAshredder column, Qiagen) and applied to the RNeasy column, rinsed and eluted. RNA concentration was calculated from the absorbance at 260 nm, and RNA purity determined from the ratio of 260 and 280 nm absorbance. Using the extracted RNA as a template, reverse transcription reactions were carried out with TaqMan Reverse Transcription Reagents (Applied Biosystems) and the RT reactions performed in a PTC-200 Peltier Thermal Cycler (MJ Research). After an initial 10 min at 25° C., the reaction mixture was incubated at 48° C. for 30 min, heated at 95° C. for 5 min, and subsequently chilled to 4° C. The TaqMan Ribosomal RNA Control Reagents Kit (Applied Biosystems) was used to detect 18s ribosomal RNA as an endogenous control.

Next, the alkaline phosphatase, cbfa1, and BMP-2 target and the endogenous rRNA control were amplified by multiplex PCR with thermal cycling parameters of 50° C. for 2 min, 95° C. for 10 min, 40 cycles of 95° C. for 15 sec, and 60° C. for 1 min, using TaqMan Universal PCR Master Mix (Applied Biosystems). The real-time PCR reactions were performed in 96-well Optical Reaction Plates (Applied Biosystems) in an ABI Prism 7300 Real Time PCR Detection System. RNA Extraction and RT-PCR protocols for the osteogenic genes were following the methods described by Perinpanayagam, H. (2002). Briefly, cultures were harvested, rinsed in PBS and total cell RNA extracted. Real-time PCR primers and probes for RUNX-2/Cbfa1 were designed with Primer Express software (Perkin Elmer) from the 294 bp of known rat sequence that correspond to exons 1 and 2 of the gene (Xiao et al. (1998) Journal of Biological Chemistry, 273(49): 32988-32994), generating an 80 bp product that overlaid an exon junction. The DNA probe was modified with the 5'-reporter dye FAM (6-carboxyfluorescein) and the 3'-quencher dye TAMRA (6-carboxy-N,N,N',N'-tetramethylrhodamine). In each reaction tube, Cbfa1 levels were normalized to 18S rRNA by calculating $\Delta Ct$, where $\Delta Ct=(FAM)Ct-(VIC)Ct$. A constant was subtracted to give $\Delta\Delta Ct$, where $\Delta\Delta t=\Delta Ct-k$ (k was adjusted to approximate the lowest $\Delta Ct$ value). The relative levels of cbfa1 were calculated as $2^{(-\Delta\Delta Ct)}$.

Figure 16:
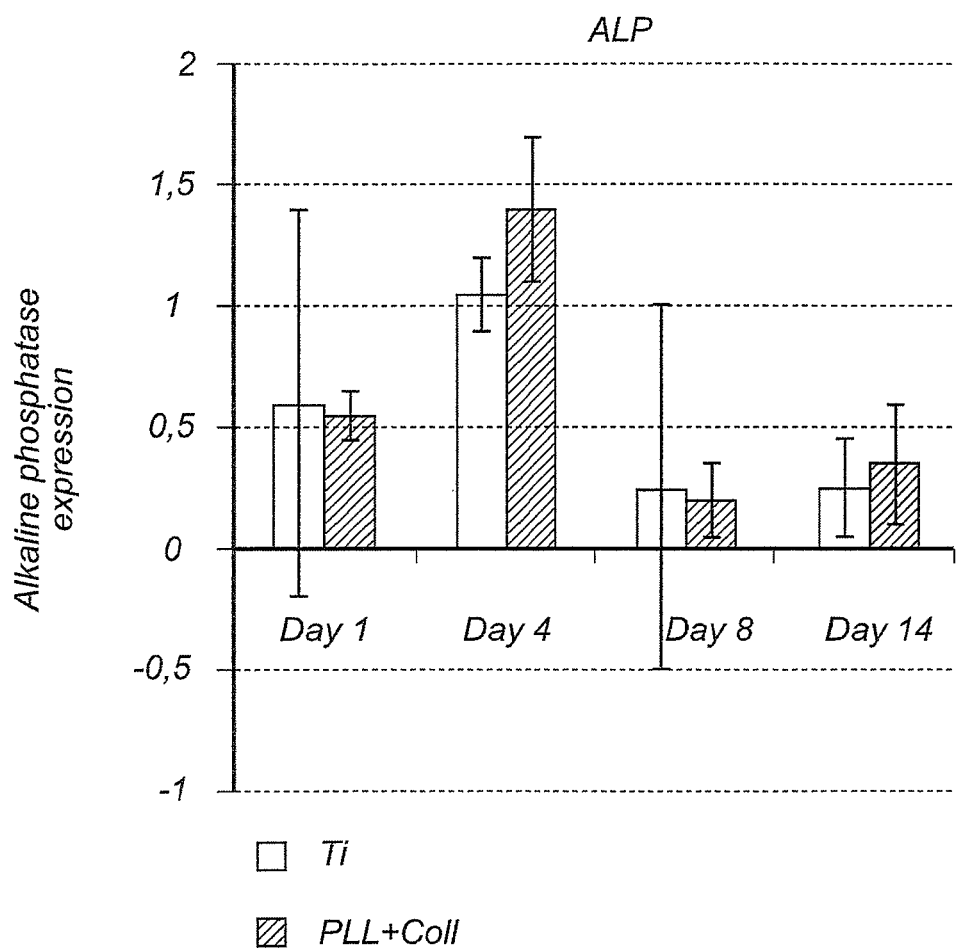
FIG. 16 is a graph showing the level of ALP expression.
Figure 17:
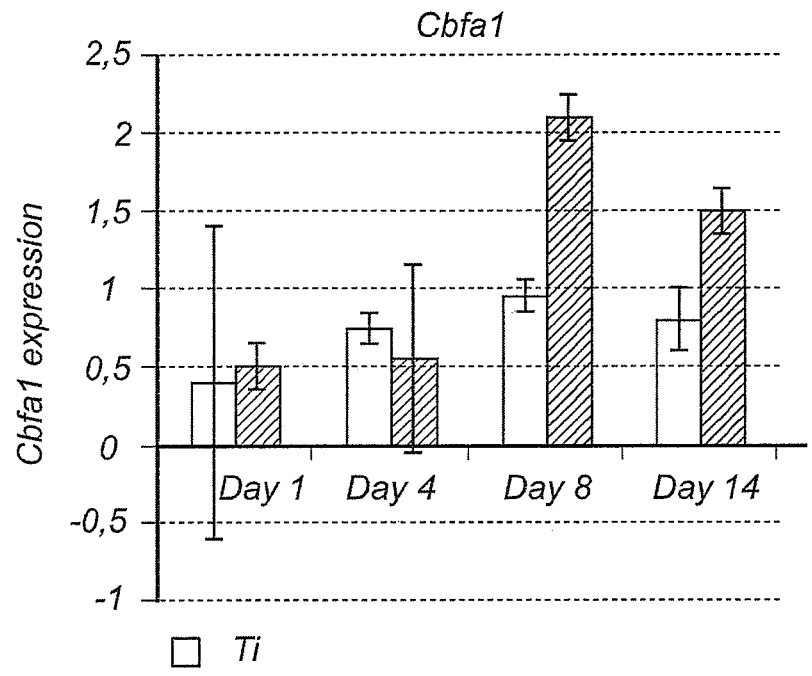
FIG. 17 is a graph showing the level of cbfa1 expression.
Figure 18:
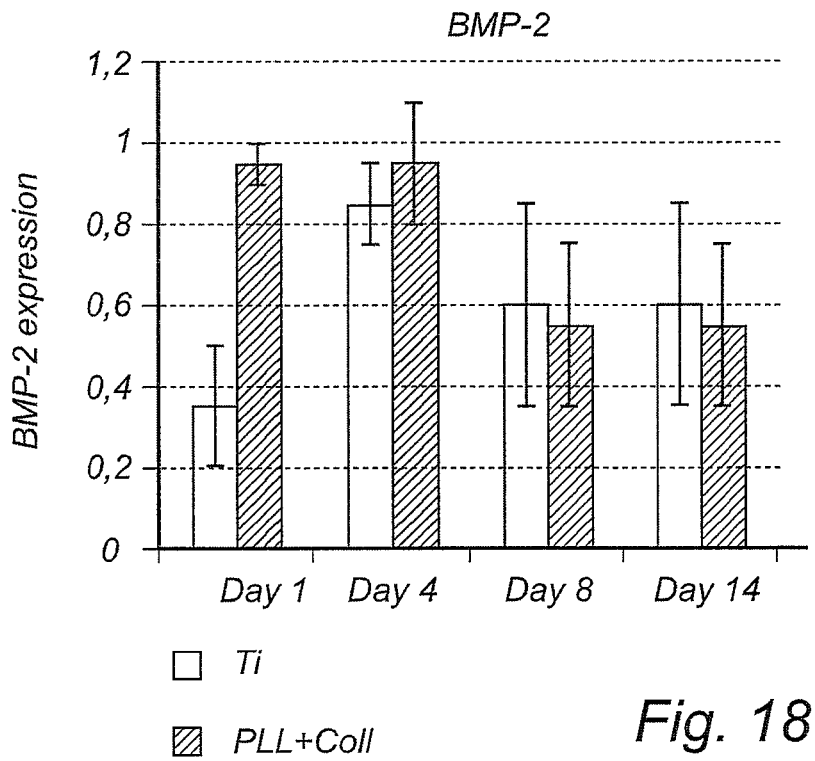
FIG. 18 is a graph showing the level of BMP-2-expression.

The level of ALP expression is shown in FIG. 16, the level of cbfa1 expression is presented in FIG. 17 and the level of BMP-2-expression is shown in FIG. 18. The following results were noted at the different time points: ALP expression peaked after 4 days on both the Ti surface and the collagen coated test surface. The collagen coated surface showed an increased level of expression compared to the Ti surface. The ALP expression appeared to decline rapidly between day 4 and day 8 but on the collagen coated surface a recovery and thus increased ALP expression was noted after 14 days of culture compared to Ti. This may suggest an inhibition of cellular differentiation (in light of the ongoing delayed cbfa1 expression (see FIG. 17) and the early elevated BMP2 (see FIG. 18). A review of the trends observed in FIG. 17 observed a rise on the collagen coated surface for the cbfa-1 steady state message starting at day 4 which was associated with a decrease ALP steady state message (see FIG. 16) at day 8, which correlates with the increase in proliferation noted at day 14 shown in FIG. 15.

3.5 Cell Activity: Protein Level Measurements

A multiplex kit was selected that provided the most objective measures of the osteogenic protein markers osteopontin and osteoprotegerin, expressed in vitro. Briefly, 50 μl cell culture supernatants were incubated with anti-human multiprotein marker beads at 4° C. for 18 hours with unbound material removed by filtration (Assay Millipore, Billerica, Mass., USA). 25 μl of anti-human multi-peptide biotin reporter was added, and reactions incubated at room temperature for 1.5 hours in the dark. 25 μl of streptavidin-phycoerythrin was added, and the plates incubated at room temperature for an additional 30 minutes. 25 μl of stop solution was added, and the plates read in a plate reader (Model 100 IS, Luminex, Austin, Tex., USA). Additionally, concentrations of cytokines IL-6 and TNF-α in each sample were extrapolated from standards (2.3-to-10,000 pg/ml) using Beadview software (Millipore, Billerica, Mass., USA).

Figure 19:
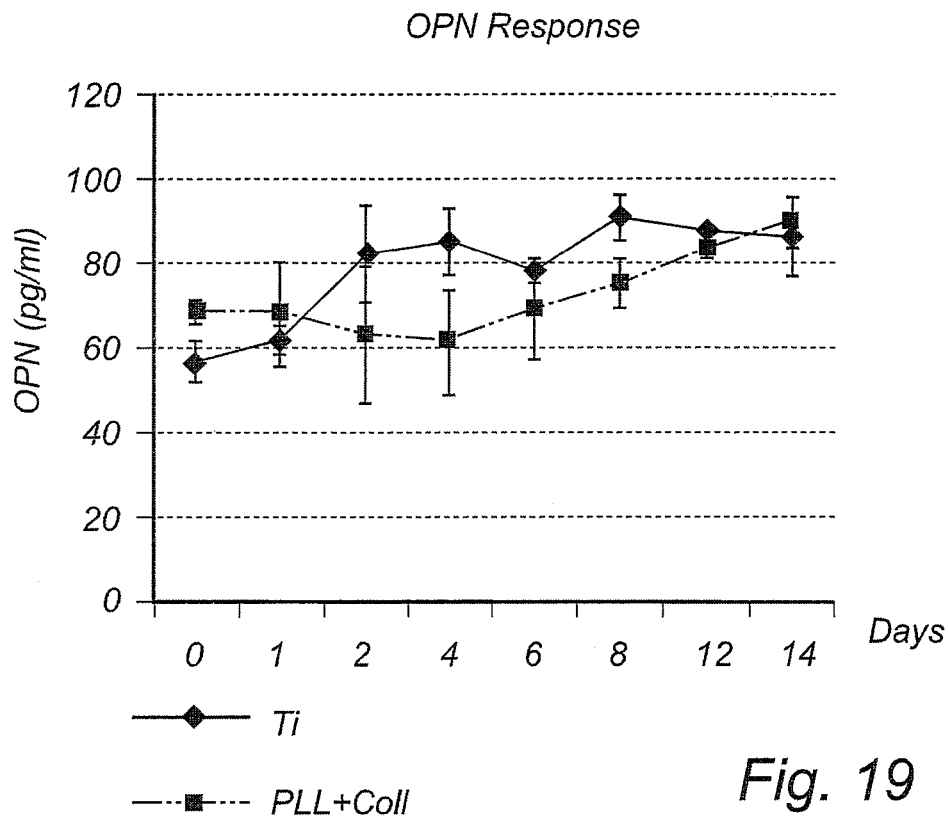
FIG. 19 is a graph showing the OPN expression.
Figure 20:
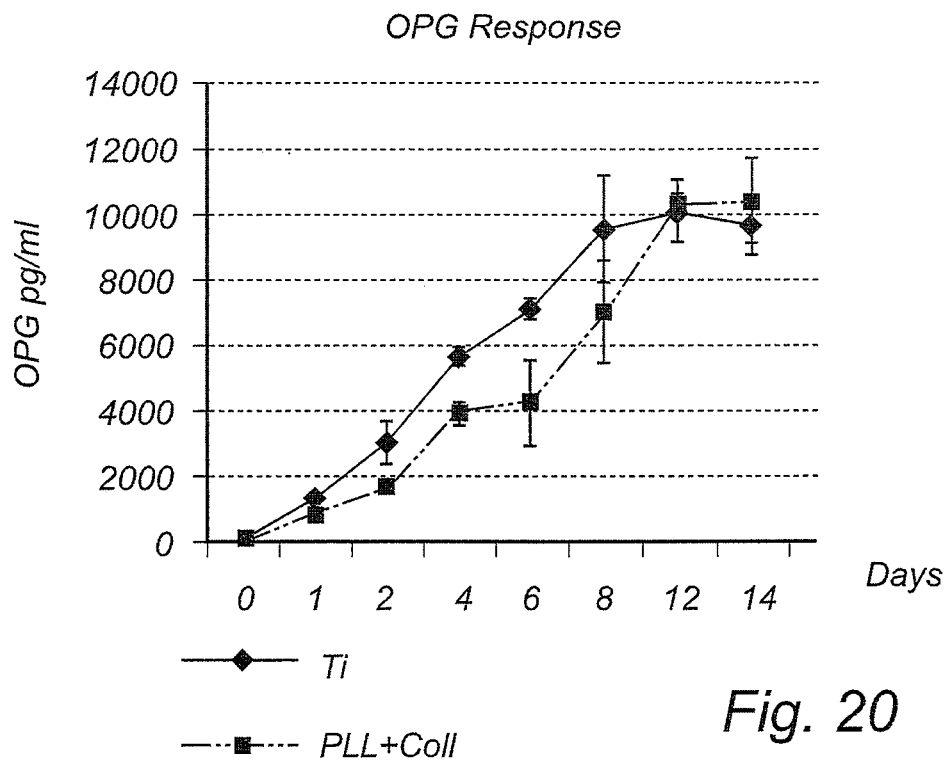
FIG. 20 is a graph showing the expression of osteoprotegerin (OPG).

The protein data used a standard proteomics kit that combined markers that are related to bone formation and bone remodeling. Expression of osteopontin (OPN), a protein involved in mineral formation, initially showed a decrease on the collagen coated surface compared to the Ti surface, but was catching up around day 12 and reaching higher expression at day 14. The OPN expression is shown in FIG. 19. FIG. 20 shows the expression of osteoprotegerin (OPG), an important bone related protein which prevents osteoclastogenesis. OPG is a competitive inhibitor of RANK and competes with the ligand for RANK, called RANK-L. In the presence of elevated OPG, RANK receptor is blocked and this prevents osteoclast differentiation, promoting the osteoblast differentiation. The OPG results show an increased expression on the Ti surface followed by the collagen coated surface catching up by day 14 (FIG. 20). For the collagen coated surface, osteoprotegerin level rose continually throughout the 14 day period.

Relatively low levels of TNF-α and IL-6 were detected for both sample surfaces, which is indicative of a normal healing process (data not shown).

3.6 Summary and Conclusions

In summary these results indicate that the HEPM cells grown on the collagen coated surface appear to have cellular proliferation encouraged over differentiation in this in vitro model. However the differentiation markers also showed an increased expression for the collagen coated surface, indicating that both the proliferation and differentiation processes are ongoing upregulated active processes occurring in the HEPM cells, with different kinetics. The ALP and BMP-2 expression levels, combined with the results of the proliferation assay, suggest that there is high cell activity on the collagen coated surface at the early timepoints (days 1 and 4), and that the proliferation acivity has slightly taken over at day 14. Simultaneously with the proliferation process however, differentiation is also in progress, as suggested by the increased cbfa1 expression level.

The person skilled in the art realizes that the present invention by no means is limited to the preferred embodiments described above. On the contrary, many modifications and variations are possible within the scope of the appended claims.

The invention claimed is:

1. A biocompatible article having a surface comprising individual collagen fibrils that do not form part of a collagen fiber attached to said surface via one or more linker molecules, wherein each of said individual collagen fibrils is attached to at least one of said one or more linker molecules at a proximal end of the fibril, and wherein each of said individual collagen fibrils has a proximal portion extending from said proximal end to a point P along said fibril, wherein, for a majority of said fibrils, each fibril is oriented so as to form an angle $\alpha_p$ in the range of 0° to 45° to the surface normal N at the point of attachment of said fibril through the one or more linker molecules to said surface.

2. The biocompatible article according to claim 1, wherein each fibril is oriented so as to form an angle $\alpha_p$ in the range of 0° to 30° to the surface normal N at the point of attachment of said fibril to said surface.

3. The biocompatible article according to claim 1, wherein said proximal portion comprises a point O along said fibril (said point O being located between said proximal end and said point P), wherein said fibril at said point O forms an angle $\alpha_O$, and wherein $\alpha_O$ is approximately equal to, or smaller than, the angle $\alpha_p$.

4. The biocompatible article according to claim 1, wherein said proximal portion is substantially straight and is oriented with an angle $\alpha_l$ in the range of from 0 to 45° in relation to the surface normal at the point of attachment of said fibril to the surface.

5. The biocompatible article according to claim 1, wherein said proximal portion extends at least 5 μm from said proximal end of the fibril.

6. The biocompatible article according to claim 1, wherein said proximal portion extends at least 20 μm from said proximal end of the fibril.

7. The biocompatible article according to claim 1, wherein the individual collagen fibrils that do not form part of a collagen fiber are oriented substantially vertical to the surface for a major portion of their length.

8. The biocompatible article according to claim 1, wherein said one or more linker molecules bind said collagen fibrils by electrostatic force.

9. The biocompatible article according to claim 1, wherein the linker is selected from poly-L-lysine, poly-D-lysine, and a covalent carbodiimide coupling.

10. The biocompatible article according to claim 1, wherein the linker is poly-L-lysine (PLL).

11. The biocompatible article according to claim 1, wherein said collagen fibrils are individual collagen fibrils that do not form part of a collagen fiber.

12. The biocompatible article according to claim 1, wherein said collagen fibrils have a diameter in the range of from 50 to 150 nm and a length in the range of from 20 to 200 pm.

13. The biocompatible article according to claim 1, having a density of collagen fibrils in the range of from 1 to 50 fibrils per $\mu m^2$.

14. The biocompatible article according to claim 1, having a density of collagen fibrils in the range of from 10 to 50 fibrils/$\mu m^2$.

15. The biocompatible article according to claim 1, wherein said collagen fibrils comprise collagen type I.

16. The biocompatible article according to claim 1, wherein said collagen fibrils consist of collagen type I.

17. The biocompatible article according to claim 1, wherein said collagen fibrils comprise human collagen.

18. The biocompatible article according to claim 1, wherein said collagen fibrils comprise bovine collagen.

19. The biocompatible article according to claim 1, wherein said surface comprises a metallic material.

20. The biocompatible article according to claim 1, wherein said surface comprises a ceramic material.

21. The biocompatible article according to claim 1, wherein said surface is intended for contact with living tissue.

22. An implant intended for implantation into the body of a human or animal, comprising a biocompatible article having a surface comprising individual collagen fibrils that do not form part of a collagen fiber attached to said surface via one or more linker molecules, wherein each of said individual collagen fibrils is attached to at least one of said one or more linker molecules at a proximal end of the fibril, and wherein each of said individual collagen fibrils has a proximal portion extending from said proximal end to a point P along said fibril, wherein, for a majority of said individual collagen fibrils, each individual collagen fibril is oriented so as to form an angle $\alpha_p$ in the range of 0° to 45° to the surface normal N at the point of attachment of said individual collagen fibril through the one or more linker molecules to said surface.

23. The implant according claim 22, wherein said surface is intended for contact with soft tissue.

24. The implant according claim 22, wherein said surface is intended for contact with bone.

25. The implant according claim 22, which is a dental implant.

26. A method of attaching individual collagen fibrils to a surface of a biocompatible article or an implant, comprising i) attaching linker molecules to said surface; and ii) attaching individual collagen fibrils to said linker molecules, wherein each of said individual collagen fibrils is attached to at least one of said one or more linker molecules at a proximal end of the fibril, and wherein each of said individual collagen fibrils has a proximal portion extending from said proximal end to a point P along said fibril, wherein, for a majority of said fibrils, each fibril is oriented so as to form an angle $\alpha_p$ in the range of 0° to 45° to the surface normal N at the point of attachment of said fibril through the one or more linker molecules to said surface.

27. The method according to claim 26, wherein the attaching step, individual collagen fibrils, comprise collagen type I.

28. The method according to claim 26, wherein step i) is performed by i-a) applying a solution comprising the linker molecules and a solvent onto the surface of the article, and i-b) removing said solvent.

29. The method according to claim 26, wherein said linker molecules comprise PLL.

30. The method according to claim 26, wherein step ii) is performed by ii-a) applying a solution comprising individual collagen fibrils and a solvent to said surface; ii-b) incubating the article having said solution applied to said surface; and ii-c) removing said solvent.

31. The method according to claim 30, wherein step ii-b) is performed by keeping the article at a temperature in the range of 4 to 40° C. for at least 10 minutes.

32. The method according to claim 30, wherein said solution comprising individual collagen fibrils has a concentration of collagen fibrils in the range of from 0.1 to 10 mg/ml.

33. The method according to claim 30, wherein said solution comprising individual collagen fibrils has a concentration of collagen fibrils in the range of from 0.5 to 5 mg/ml.

34. The method according to claim 26, wherein the density of collagen fibrils on said surface after step ii) is in the range of from 2 to 50 fibrils/$\mu m^2$.

35. The method according to claim 26, wherein the density of collagen fibrils on said surface after step ii) is in the range of from 10 to 50 fibrils/$\mu m^2$.

* * * * *